(12) United States Patent
Goldberg et al.

(10) Patent No.: US 7,186,115 B2
(45) Date of Patent: Mar. 6, 2007

(54) ADVANCED THERMOPLASTICS FOR ORTHODONTICS

(75) Inventors: Artie J. Goldberg, West Hartford, CT (US); Charles J. Burstone, Farmington, CT (US)

(73) Assignee: University of Connecticut, Farmington, CT (US)

( * ) Notice: Subject to any disclaimer, the term of this patent is extended or adjusted under 35 U.S.C. 154(b) by 313 days.

(21) Appl. No.: 10/612,511

(22) Filed: Jul. 2, 2003

(65) Prior Publication Data

US 2004/0013994 A1 Jan. 22, 2004

Related U.S. Application Data

(60) Provisional application No. 60/393,791, filed on Jul. 3, 2002.

(51) Int. Cl.
*A61C 3/00* (2006.01)
(52) U.S. Cl. ........................................ 433/18

(58) Field of Classification Search ................. 433/8, 433/18, 20, 22
See application file for complete search history.

(56) References Cited

U.S. PATENT DOCUMENTS

| 4,717,341 A | 1/1988 | Goldberg et al. |
| 5,174,753 A * | 12/1992 | Wool .............................. 433/8 |
| 5,622,495 A | 4/1997 | Chikami et al. |
| 5,869,592 A | 2/1999 | Gagne et al. |
| 5,886,130 A | 3/1999 | Trimmer et al. |
| 6,087,467 A | 7/2000 | Marrocco et al. |
| 6,267,590 B1 | 7/2001 | Barry et al. |

* cited by examiner

*Primary Examiner*—Melba Bumgarner
(74) *Attorney, Agent, or Firm*—Alix, Yale & Ristas, LLP

(57) ABSTRACT

An orthodontic appliance including at least one orthodontic component comprising a thermoplastic polymer. In some embodiments the thermoplastic polymer is a rigid backbone polymer including at least one of a compatibilizing side roup or a solubilizing side group. The thermoplastic polymer may be heat processed to form the orthodontic component.

32 Claims, 14 Drawing Sheets

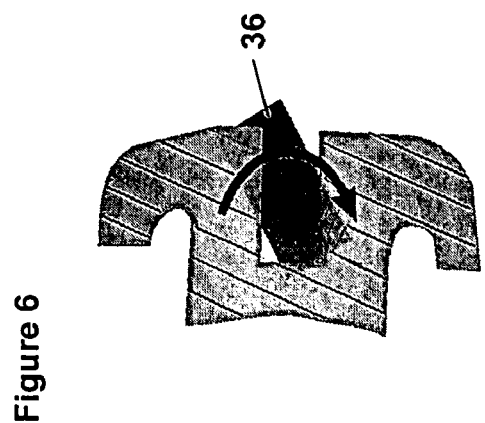
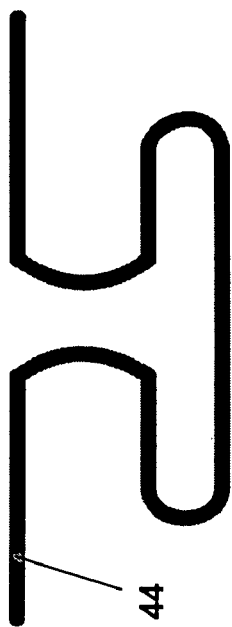
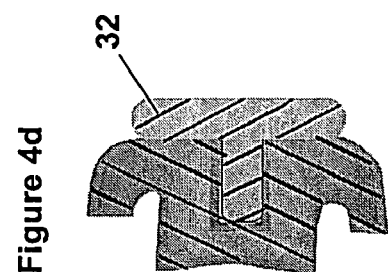
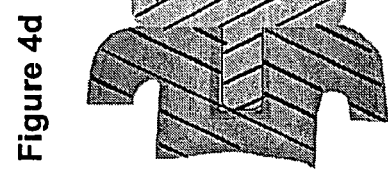
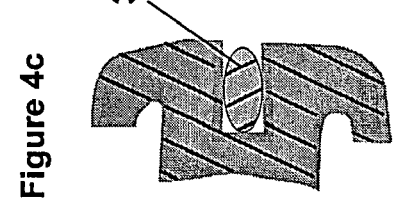
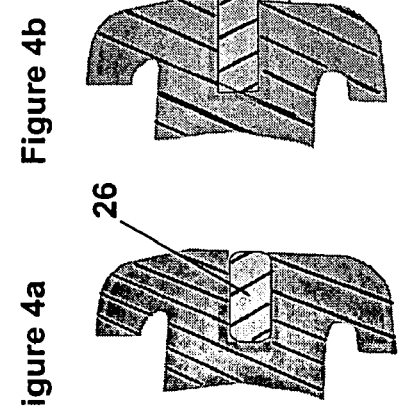
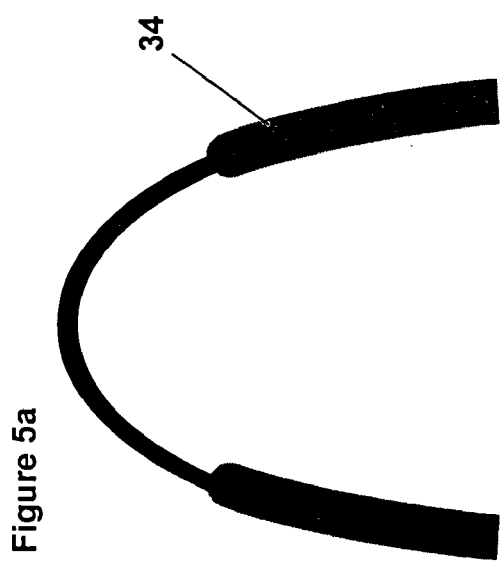

A = 3.0 mm (0.118 in)
B = 2.0 mm (0.079 in)
C = 0.61 mm (0.024 in)
D = 0.51, 0.99, 1.50, 2.01 mm (0.020, 0.039, 0.059, 0.079 in)
E = 0.56 mm (0.022 in)
F = 1.40 mm (0.055 in)
G = 5.49 mm (0.216 in)
H depends on value of D

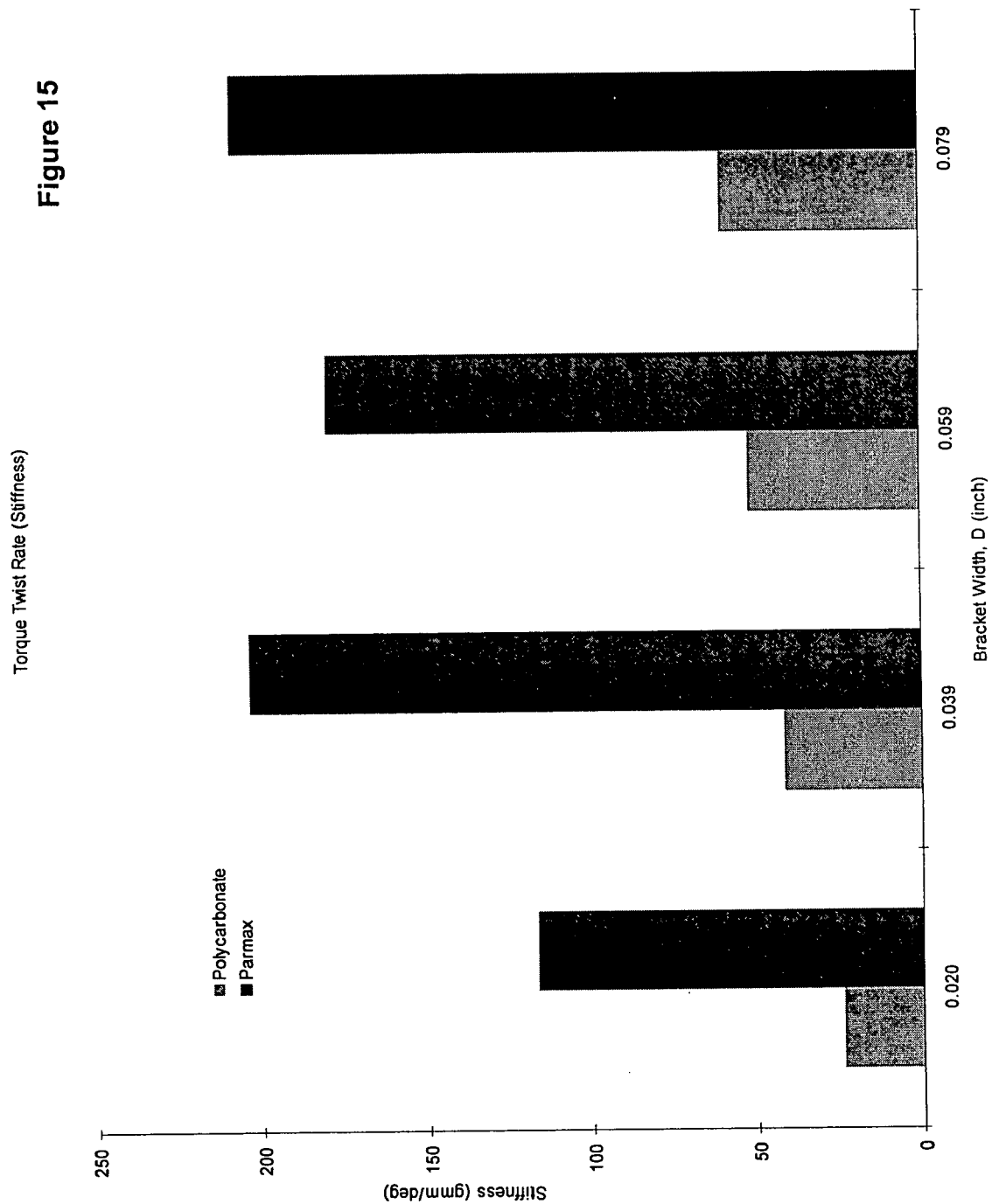

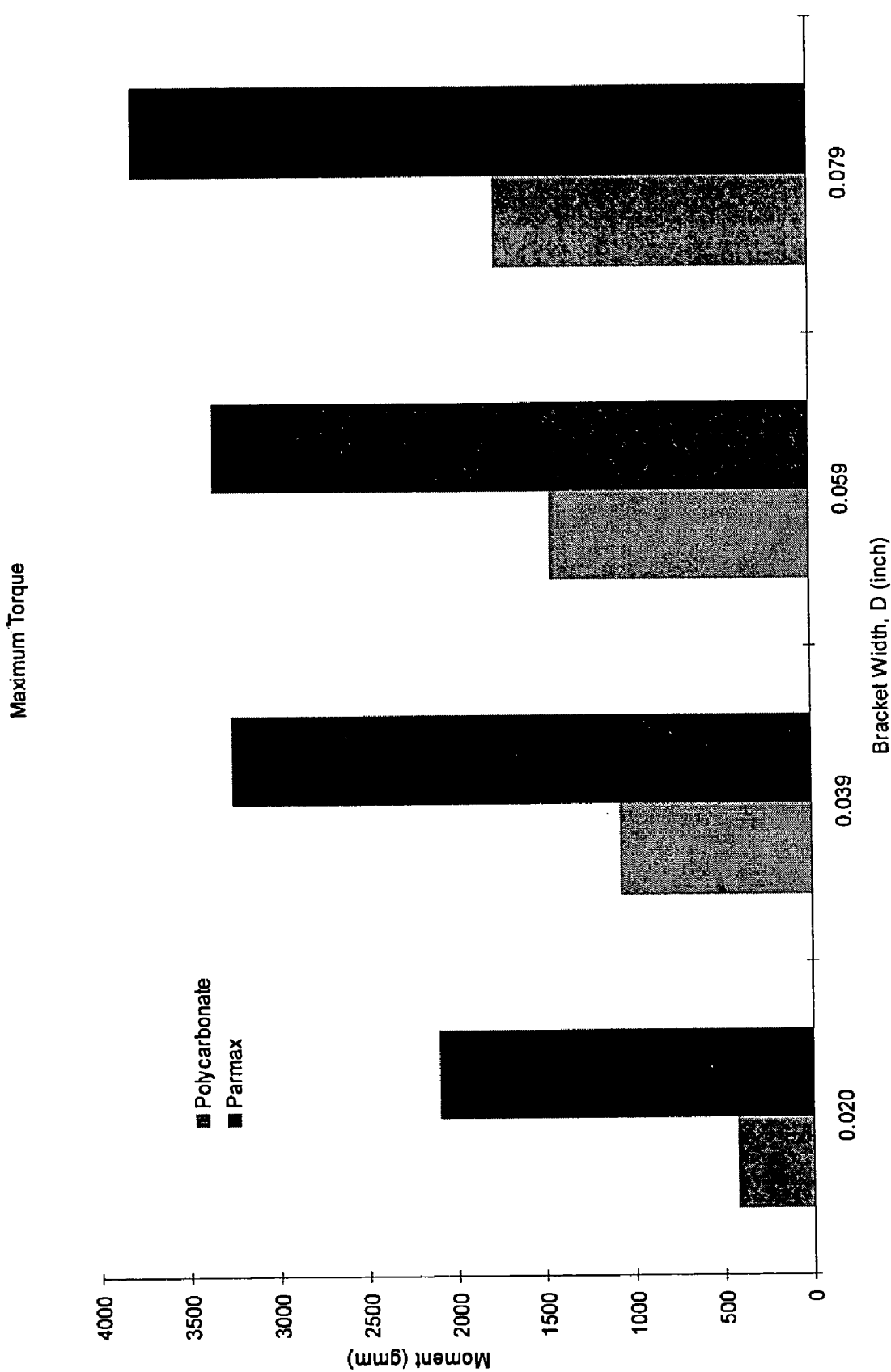

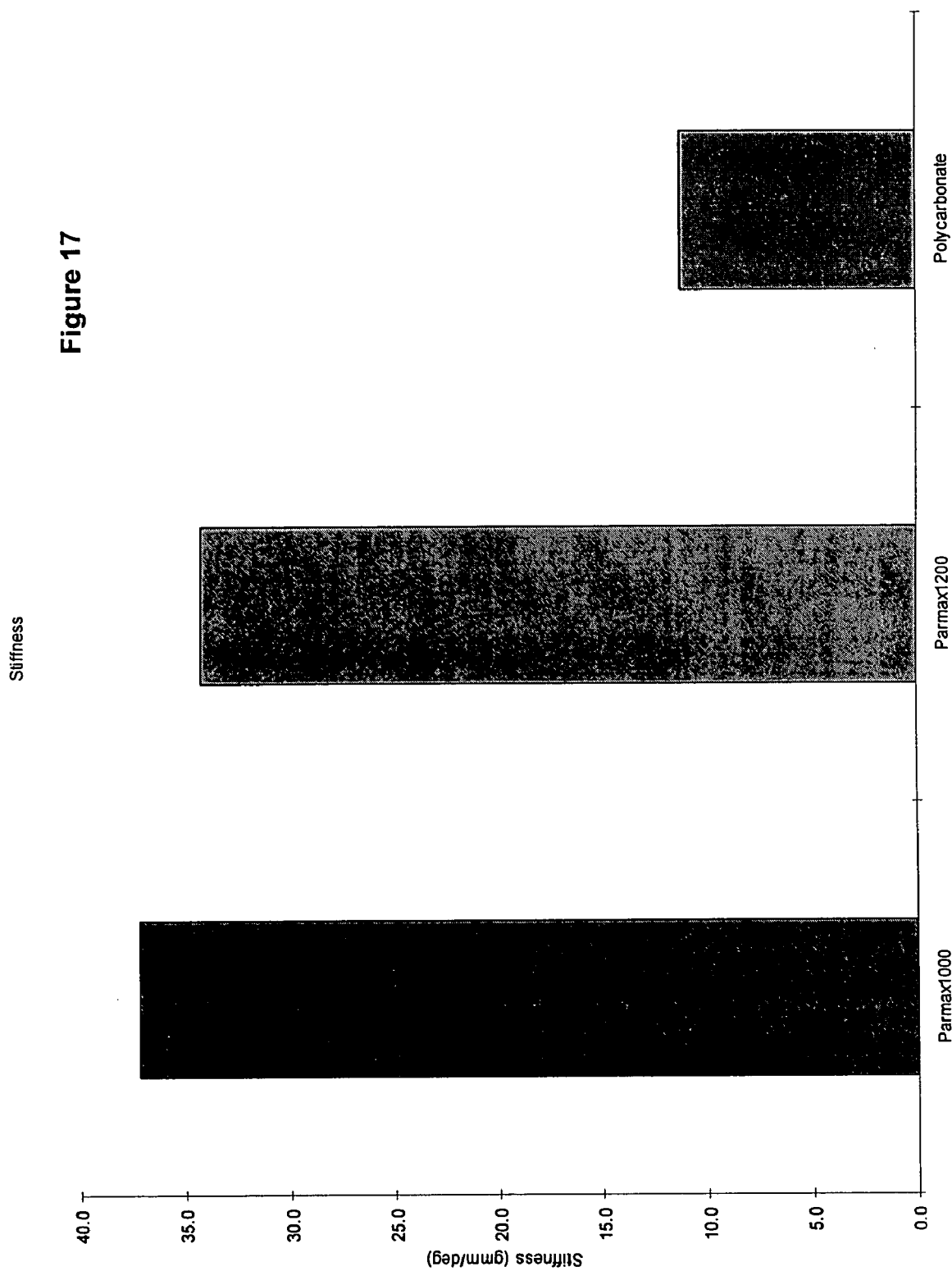

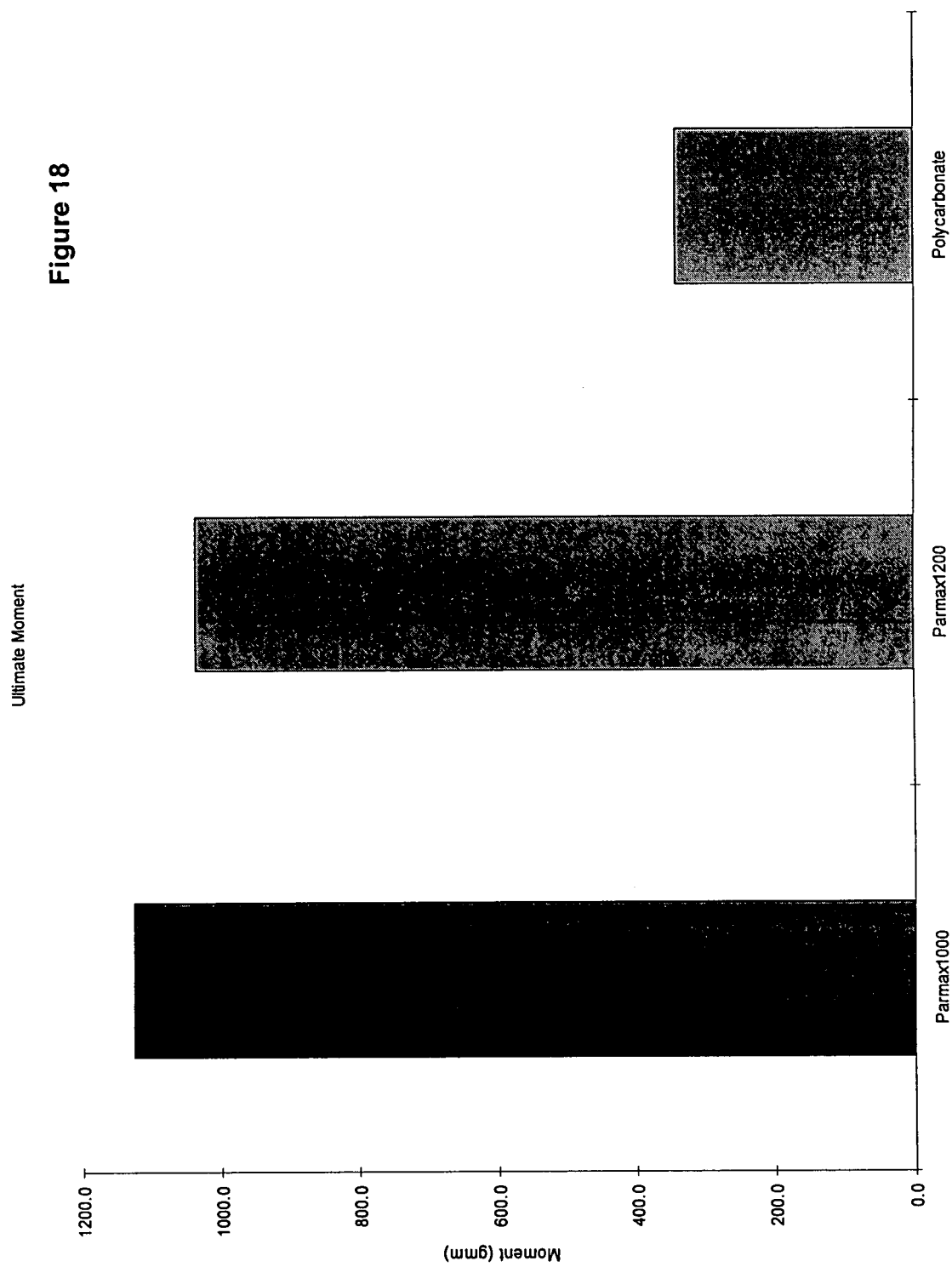

ADVANCED THERMOPLASTICS FOR ORTHODONTICS

The present application claims the benefit of U.S. Provisional Patent Application No. 60/393,791 filed Jul. 3, 2002.

FIELD OF THE INVENTION

The present invention relates generally to polymer comprising orthodontic devices. One aspect of the present invention is more particularly concerned with new and improved polymer comprising orthodontic components and appliances.

BACKGROUND OF THE INVENTION

As is well known, orthodontic appliances are used to move or manipulate certain teeth to correct irregularities and/or abnormalities in their relationships with surrounding members. Orthodontic appliances include systems comprising wires and brackets as well as systems comprising removable aligners. This manipulation is achieved by the application of designed force systems to selected teeth. The forces for these systems are provided by a force delivery component such as an arch wire or spring. The wire is elastically deformed, or activated, to absorb energy. The wire slowly releases this energy as it deactivates and returns to the relaxed condition. The released energy is applied to selected teeth, for instance by interaction of the loaded wire with brackets attached to the teeth, to provide the desired tooth movement.

Tooth movement can best be achieved by producing an optimal force system capable of delivering relatively light but continuous corrective forces. Some desirable biomechanical characteristics of the orthodontic force system include low to moderate force magnitude, constancy of force magnitude during deactivation and accurate location of the force application point. The use of a low to moderate force magnitude will allow the teeth to move rapidly and relatively painlessly with minimum tissue damage. A constant force magnitude over time will provide maximum tissue response. Additionally, if the orthodontic appliance releases force too rapidly, it becomes more difficult to accurately produce the desired effect, requiring more frequent adjustments to maintain the force at some minimum desired level.

There are several additional criteria that are important for orthodontic appliances in general. For example, the orthodontic material must be non-toxic, resistant to the corrosive environment within a patient's mouth and available in desired shapes and dimensions. Some other important parameters, especially for orthodontic force delivery components, include strength, elastic deformation, yield strength, stiffness, formability and joinability. More recently, the aesthetic appearance of orthodontic components has become very important, with many patients expressing a strong preference for orthodontic components and appliances that are less visually apparent against the patient's teeth.

Elastic deformation or "spring back" is a measure of the amount of deflection or activation that the wire or other component can sustain and still be totally elastic, that is, to recover to its original shape and position. The elastic deformation of an orthodontic component is fundamentally proportional to its ratio of flexure strength to flexure modulus; or similarly its ratio of tensile yield strength to modulus of elasticity. The higher the ratio of yield strength to modulus, the greater the elastic deformation. Design factors also affect elastic deformation, for example, the elastic deformation of round wire varies inversely as the first power of the diameter and the second power of the length of the wire. Elastic deformation is important because it determines the distance over which an appliance can provide an effective force system before readjustment is necessary. Appliances that can sustain larger elastic deformation (deflection) can more readily engage teeth that are severely malposed.

Yield strength must be high enough to assure achieving desired force levels for tooth movement and preventing appliance failure associated with permanent deformation. The lack of adequate yield strength can not be corrected by design changes such as increase in size or bulk because of size limitations in the oral cavity. Metals have traditionally been used in orthodontics because in the necessary cross-sections they provide desirable force levels that other categories of structural materials, such as engineering plastics, have not been able to provide.

Stiffness is the ratio of force/unit activation. The stiffness or rigidity of an appliance varies significantly with appliance design, for example, stiffness varies as the fourth power of the diameter for round wire. For rectangular wire, stiffness varies as $bd^3$, where b is the base or cross-sectional dimension perpendicular to the force and and d is the depth or cross-sectional dimension parallel to the force. Wires of unique cross-sections, such as polygonal, offer different stiffnesses, and hence different forces, in different planes. Although not available with metal appliances, it is desirable for an appliance to have unique cross-sectional shapes that give greater control over tooth movement by varying force as required in the three dimensional planes.

The stiffness of an appliance component, when stiffness is linear in the range of use, is a primary determinant of the force that can be applied to teeth during manipulation. Greater stiffness results in more force for each unit of activation. Generally, low stiffness orthodontic components are required for active tooth movement and high stiffness components for passive holding components. High stiffness may be required for small deflection applications. For example, if a tooth were 4 mm out of alignment and 100 g of force is needed, 25 g/mm would be a low stiffness and 1,000 g/mm would be a high stiffness.

Some orthodontic components, such as a wire, require sufficient ductility to be formed to a desired customized shape for a particular patient. Additionally, the wire has to be joinable to other wires or components, while retaining its strength and elasticity characteristics. Naturally, the wire must be available in a variety of desired cross-sectional shapes and dimensions as variability in cross-sectional shape can allow greater potential control of orthodontic force systems. All orthodontic wires have conventionally had either rectangular or circular cross sections.

Some orthodontic components, such as attachments, that translate the force from the wire directly to the tooth have additional criteria that have to be considered. For example, the design, geometry and overall dimensions of an attachment such as a bracket are important for both its ease of manipulation as well as its ability to help contribute to effective application of the orthodontic force system. Attachments may be bonded directly to the tooth surface or mechanically fastened using a band that typically circumscribes the entire tooth. An attachment that is bonded may have certain functional shapes and contours on the surface contacting the tooth in order to aid adhesion. Attachments should be easy to fabricate or manufacture. Attachments must have sufficient strength to transfer force to the joined tooth without attachment deformation or fracture. Additionally, it is desirable for the bracket to be comprised of a material that provides a low level of friction to wires within the slot. Aesthetics of attachments are again very important to some patients.

There have been attempts to use material selection in conjunction with appliance design to control orthodontic force systems. Over the years dental practitioners have used orthodontic force delivery components made from gold alloys, stainless steel alloys, nickel-titanium memory type alloys of the type described in U.S. Pat. No. 4,037,324 and beta titanium alloys of the type described in U.S. Pat. No. 4,197,643 in an effort to design orthodontic components that can impart a desired force system. While the above materials have been successfully used for orthodontic applications, some deficiencies remain.

Orthodontic component aesthetics is an increasingly important consideration, particularly for labial appliances and components. Metal components have a characteristic gray or silver color that is quite obvious against the color background of the tooth structure and aesthetically objectionable to many patients. The use of clear or tooth-colored components and appliances would be considerably more aesthetically pleasing to many patients. Attempts have been made to overcome the aesthetic deficiencies of metal orthodontic components. Tooth colored plastic coatings have been applied to the metal components. Such coatings can lose adhesion to the underlying metal surface and peel off; exhibit an undesirably high amount of friction when used with metal or ceramic brackets and are relatively soft and can be scraped or gouged by contact with harder surfaces.

Metallic orthodontic components have also specifically been identified as a problem area for the nuclear magnetic resonance diagnostic procedure, since metals do not exhibit the requisite radiolucency and interfere with the resulting images.

There have also been attempts to use material selection to improve characteristics of other orthodontic components. Brackets have been fabricated from ceramic materials in an attempt to provide a more aesthetically pleasing appliance. However, ceramic brackets, while available, are expensive; are not available in more complex shapes and sizes; are brittle; and are very hard and can wear contacting teeth. Ceramic brackets may also be difficult to debond, leading to tooth enamel fracture.

Another approach to orthodontic tooth movement is the use of a removable appliance, such as an aligner, in place of wires and brackets. Such aligners can be very aesthetic and "patient friendly" since they are removable by the patient and require no bonding of attachments. One limitation of current materials with respect to aligners is the occurrence of permanent deformation adjacent to the imprint of the final crown position, which does not allow exact tooth movement because the shape of the aligner has been altered and no longer applies the required force. This permanent deformation is related to inadequate mechanical properties of available materials used in removable appliances, for example yield strength and modulus.

It is generally believed that thermoplastic polymers such as polymethylmethacrylate (PMMA) or polycarbonate and even high strength polymers such as polyetheretherketone (PEEK) do not possess the requisite flexural strength, modulus and elastic deformation desirable, or in some cases necessary, for use as a force delivery component. Table 1 lists the mechanical properties of some known high strength engineering polymers as well as properties for some metals useful in orthodontic use.

TABLE 1

| Material | Flexure Modulus, GPa | Flexure Strength, MPa Yield | Tensile Modulus, GPa | Tensile Strength, MPa Yield | Tensile Strength, MPa Ultimate |
|---|---|---|---|---|---|
| Polybenzimidazole (PBI) | 6.6 | 221 | 5.8 | | 160 |
| Polyamide-imide (PAI) | | | 5.2 | | 185 |
| Polyphenylene sulfide (PPS) | 3.8 | 96 | 3.8 | | 65 |
| Polyetheretherketone (PEEK) | 4.1 | 170 | 3.5 | 97 | 120 |
| Polyether-imide (PEI) | 3.3 | 118 | 3.3 | | 103 |
| Polymethylmethacrylate (PMMA) | 2.3 | 91 | 2.5 | 51 | 53 |
| Polycarbonate (PC) | 2.8 | 88 | 2.3 | 62 | 70 |
| Acrylonitrile-butadiene-styrene (ABS) | 2.5 | 83 | 2.3 | | 50 |
| Polyamides (nylon) | 1.8 | 80 | 1.9 | 60 | 75 |
| Thermoplastic Polyurethane | 0.5 | | 1.2 | | 37 |
| Nickel-Titanium | | | 41.4 | | 1489 |
| Beta Titanium | | | 71.7 | | 1276 |
| Stainless Steel | | | 179.0 | | 2117 |

Brackets have been fabricated from polycarbonate materials in an attempt to provide a more aesthetically pleasing appliance. However, polycarbonate brackets cannot resist the high stress magnitudes frequently encountered in orthodontics so that the bracket slot distorts or spreads apart under torque loading well below the levels desirable for clinical use. In addition, polycarbonate brackets have tying wings that have been known to fail. Polycarbonate as an orthodontic material can also stain from contact with food.

More recently, highly fiber reinforced composite materials such as those described in U.S. Pat. No. 4,717,341 have been proposed for use in orthodontics. Such highly fiber reinforced composite materials show promise in this application, however, these materials presently are anisotropic, are somewhat difficult to form into complex shapes, require effective coupling of the high strength reinforcing phase into the polymer matrix and have low ductility.

Some Definitions Used in the Specification

The following terms will have the given definitions unless otherwise explicitly defined.

Elastic deformation or spring back—the amount of deflection or activation that the wire or other component can sustain and still be totally elastic, that is, to recover to its original shape and position.

Filler material—Particles, powder or other materials having having approximately equal dimensions in all directions. Filler material is added to a polymer primarily to enhance polymer properties such as wear resistance, mechanical properties or color.

Neat—Without admixture or dilution, that is substantially free of materials such as additives, filler materials, other polymers, plasticizers and reinforcing agents.

Non-Thermoplastic polymer—Any polymer which does not fall within the definition of a thermoplastic polymer.

Orthodontic appliance—A device used for tooth alignment, occlusal correction and non-surgical jaw alteration. Appliances can be fixed or removable. Removable appliances, such as aligners, are inserted and removed by the patient.

Orthodontic attachment—Brackets, tubes or other shapes bonded to a tooth or to a band that joins an orthodontic wire with the tooth.

Orthodontic auxiliary—Items added to supplement an appliance, including springs separate from the arch wire and hooks and buttons joined to a wire or tooth.

Orthodontic component—Any part of a fixed or removable appliance, for example attachments, wires, ligating mechanisms and auxiliaries.

Orthodontic force delivery component.—Any part of an orthodontic appliance that is capable of storing energy for tooth movement.

Orthodontic ligating mechanism—Mechanism such as metal ligature wires, elastomeric rings or caps for joining wires to an attachment.

Orthodontic wire—A force delivery component of the appliance.

Polymer—A long chain of covalently bonded, repeating, organic structural units. Generally includes, for example, homopolymers, copolymers, such as for example, block, graft, random and alternating copolymers, terpolymers, etc, and blends and modifications thereof. Furthermore, unless otherwise specifically limited, the term "polymer" includes all possible geometric configurations. These configurations include, for example, isotactic, syndiotactic and random symmetries.

Reinforcing agent—a filament, fiber, whisker, insert, etc. having a length much greater than its cross sectional dimensions. Reinforcing agents are primarily used to increase the mechanical properties of a polymer.

Stiffness—The ratio of a steady force acting on a deformable elastic material to the resulting displacement of that material.

Thermoplastic polymer—A polymer that is fusible, softening when exposed to heat and returning generally to its unsoftened state when cooled to room temperature. Thermoplastic materials include, for example, polyvinyl chlorides, some polyesters, polyamides, polyfluorocarbons, polyolefins, some polyurethanes, polystyrenes, polyvinyl alcohol, copolymers of ethylene and at least one vinyl monomer (e.g., poly (ethylene vinyl acetates), cellulose esters and acrylic resins.

Unreinforced—A material with substantially no reinforcing agent.

SUMMARY OF THE INVENTION

Briefly, one aspect of the invention is an orthodontic component comprised of a thermoplastic polymer wherein the thermoplastic polymer in the neat resin form has an unreinforced tensile strength of at least about 150 MPa and an unreinforced tensile modulus of at least about 4 GPa. In one embodiment the component comprises a rigid backbone polymer. In another embodiment the inventive component is an orthodontic force delivery component.

Another aspect of the invention is an orthodontic appliance comprised of a thermoplastic polymer wherein the thermoplastic polymer in the neat resin form has an unreinforced tensile strength of at least about 150 MPa and an unreinforced tensile modulus of at least about 4 GPa. In one advantageous embodiment all of the components of the appliance are comprised of a rigid backbone polymer. In another embodiment the inventive orthodontic appliance includes components comprised of a rigid backbone polymer as well as components comprised of other materials.

Yet another aspect of the present invention is the provision of an orthodontic component or an orthodontic appliance having an improved aesthetic appearance. The components and appliances are fabricated from a thermoplastic polymer having a refractive index of about 1.66 to about 1.70. The thermoplastic polymer ranges from transparent to translucent and may include fillers, additives or other materials to approximate the color of a patient's tooth. In one embodiment the component comprises a rigid backbone polymer.

Still another aspect of the invention is a method of manufacturing an orthodontic component comprising heating a thermoplastic polymer to a softened state and forming the softened thermoplastic polymer into an orthodontic component.

In general, unless otherwise explicitly stated the material of the invention may be alternately formulated to comprise, consist of, or consist essentially of, any appropriate components herein disclosed. The material of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

A better understanding of the invention will be obtained from the following detailed description and the accompanying drawings as well as from the illustrative applications of the invention including the several components of the invention and the relation of one or more of such components with respect to each of the others as well as to the features, characteristics, compositions, properties and relation of elements described and exemplified herein.

BRIEF DESCRIPTION OF THE DRAWINGS

Other objects and advantages of the invention will be evident to one of ordinary skill in the art from the following detailed description made with reference to the accompanying drawings, in which:

FIGS. 4a–4d are cross sectional representations illustrating some embodiments of some inventive orthodontic components.

FIGS. 5a–5b are schematic illustrations showing some shaped embodiments of inventive force delivery components.

FIG. 6 is a cross sectional illustration of one embodiment of an inventive torsional force delivery component releasing energy to one embodiment of an inventive bracket.

FIG. 12b is a front view of the tube of FIG. 12a.

FIG. 15 is a graph of stiffness and bracket width for some inventive and comparative (polycarbonate) brackets.

FIG. 16 is a graph showing maximum torque for some inventive and comparative (polycarbonate) brackets.

FIG. 17 is a graph showing maximum stiffness for some inventive and comparative (polycarbonate) wires.

FIG. 18 is a graph showing maximum moment for some inventive and comparative (polycarbonate) wires.

DETAILED DESCRIPTION OF THE INVENTION

Figure 2:
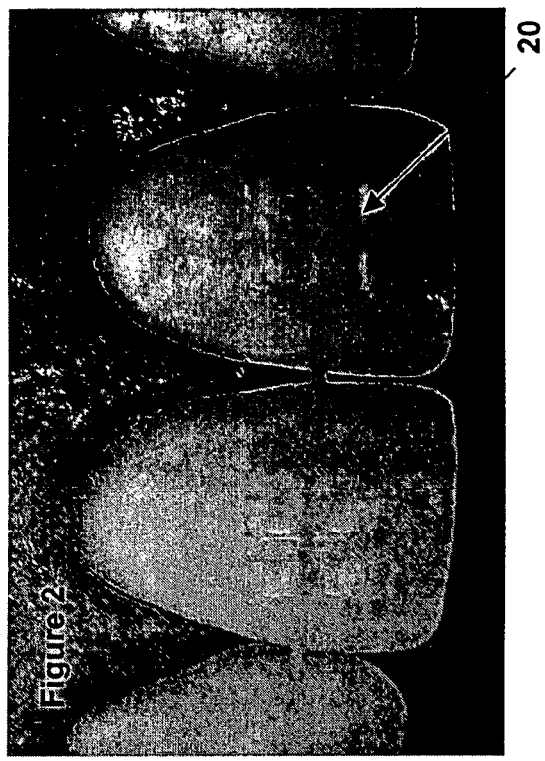
FIG. 2 is an illustration of a portion of one embodiment of an installed orthodontic appliance showing a pair of conventional brackets with an inventive force delivery component engaged within slots in each of the brackets.
Figure 11:
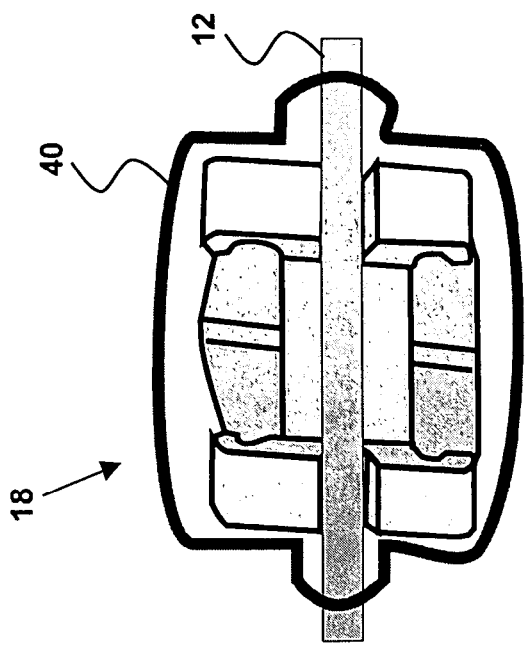
FIG. 11 is a front view of one embodiment of the invention illustrating an inventive ligating spring securing an inventive wire within a slot of a bracket.
Figure 13:
FIG. 13 is a cross sectional representation of one embodiment of an inventive orthodontic auxiliary including a hook.

In contrast to the prevailing knowledge in the art, it has now been discovered that certain thermoplastic polymers surprisingly do possess the requisite combination of tensile strength, tensile modulus and elastic deformation to provide orthodontic force magnitudes at least at the lower to intermediate range of forces produced by conventional metal appliances. Thus one aspect of the present invention is the use of thermoplastic polymer materials to produce an orthodontic component, including (with reference to FIG. 1), for example, a force delivery component 12, an attachment 14, an auxiliary 16 (shown in FIG. 13) and a ligating mechanism 18 (shown in FIG. 11). The inventive components can be used, with or without conventional orthodontic components, to form novel orthodontic appliances 20 such as shown in FIG. 2.

One class of polymers useful in the present invention are the rigid backbone polymers. As used herein, the term rigid backbone polymer encompasses any of a "rigid-rod polymer", a "segmented rigid-rod polymer", a "semi-rigid-rod polymer" or a combination thereof. Rigid backbone polymers have a backbone at least partially comprising arylene or heteroarylene moieties covalently bonded to each other. U.S. Pat. No. 5,886,130 (Trimmer et al.) and U.S. Pat. No. 6,087,467 (Marrocco, III et al.), the contents of which are incorporated by reference herein, provide further description of some rigid backbone polymers. Parmax® 1000 and Parmax® 1200, available from Mississippi Polymer Technologies, Inc. of Bay St. Louis, Miss., are representative of some rigid backbone polymer materials found useful in practice of the invention. Rigid backbone polymers have a surprisingly unique balance of properties for use in orthodontic applications, that require high mechanical properties, formability, thermoplastic processing capability and sometimes translucency. In orthodontic applications, the mechanical properties of unreinforced rigid backbone polymers are sufficient to deliver the necessary biomechanical forces, a level only possible with certain other polymers when a second phase, high strength reinforcement, such as fibers, are used. The absence of reinforcing fibers or particles provides high ductility and ease of processing both for the clinician and the manufacturer, while maintaining a high degree of clarity, making for outstanding aesthetics. In addition, since the subject polymer is a thermoplastic there is for the first time the potential of using various thermal processing methods, such as injection molding, compression molding or extrusion to form orthodontic components with various shapes and geometries. For example, the geometry and size of an inventive archwire can be varied along its length, creating endless, novel possibilities for control of forces.

Rigid-rod polymers are comprised of phenylene monomer units joined together by carbon-carbon covalent bonds, wherein at least about 95% of the bonds are substantially parallel to each other. Preferably, the covalent bonds between monomer units are 1,4 or para linkages so that each monomer unit is paraphenylene. Each paraphenylene monomer unit can be represented by the

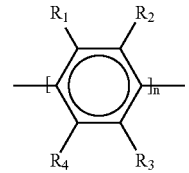

following structure.

This molecular arrangement of paraphenylene groups, while able to rotate about its long axis, cannot bend or kink as is possible with most other engineering polymer backbones, imparting high mechanical properties.

A polymer consisting only of rigid-rod macromonomers would not be soluble, making synthesis very difficult and thermal processing impossible. Accordingly, each of $R_1$, $R_2$, $R_3$ and $R_4$ is independently chosen from H or an organic solubilizing group. The number and size of the organic solubilizing groups chosen being sufficient to give the monomers and polymers a significant degree of solubility in a common solvent system. As used herein, the term "soluble" means that a solution can be prepared containing greater than 0.5% by weight of the polymer and greater than about 0.5% of the monomer(s) being used to form the polymer. As used herein, the term "solubilizing groups" means functional groups which, when attached as side chains to the polymer in question, will render it soluble in an appropriate solvent system. Parmax® 1000 (poly-1,4 (benzoylphenylene)), available from Mississippi Polymer Technologies, Inc., is one example of a rigid-rod polymer.

Segmented rigid-rod polymers are polymers that comprise both rigid-rod segments comprised of rigid-rod monomer units (defined above) and non-rigid-rod segments in the backbone of the polymer. The segmented rigid-rod polymer has the following structure:

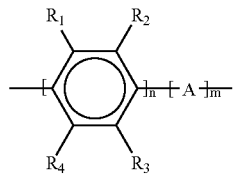

wherein

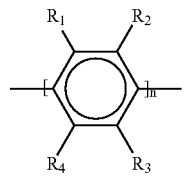

represents the rigid-rod monomer segment described above and the repeating [A] units are other than the rigid-rod segments. The average length of the rigid-rod segment (n) is about 8 monomer units, while the average length of the non rigid-rod segment (m) is at least 1. Each of $R_1$, $R_2$, $R_3$ and $R_4$ is independently chosen from H or an organic solubilizing group.

Semi-rigid-rod polymers include a backbone comprising (1,4) linked paraphenylene monomer units and non-parallel, phenylene monomer units. Preferably, the non-parallel phenylene monomer units comprise (1,3) or meta phenylene polymer units. By introducing non-parallel phenylene repeat units, specifically meta-phenylene repeat units, solubility and processability can be maintained with fewer solubilizing groups ($R_1$–$R_4$) than are required for rigid-rod polymers. These semi-rigid-rod polymers, with fewer parallel paraphenylene units in the backbone are at most semi-rigid and do not have the extremely high viscosity characteristics of rigid-rod polymers, yet still have mechanical properties superior to standard engineering thermoplastics. One example of a para and meta structure is a random co-polymer of benzoyl appended 1,4-phenylene and 1,3-phenylene, which is similar in structure to the commercial polymer Parmax® 1200 available from Mississippi Polymer Technologies, Inc.

In some embodiments, the properties for rigid backbone polymers such as tensile strength and tensile modulus are dependent on the chemical structure of the polymer and processing conditions used to prepare the polymer. Alteration of the monomer components and monomer component ratios is believed to allow lower values for properties such as tensile strength and tensile modulus. For example, the monomer component ratios could be altered to achieve a rigid backbone polymer having a neat resin tensile strength of about 150 MPa or lower and a neat resin tensile modulus of about 4 GPa or lower.

All three classes of rigid backbone polymers use solubilizing side groups to some extent. It is well known that it is difficult a priori to select an appropriate solvent, thus various factors will determine the effectiveness of the selected solubilizing groups. Such factors include the nature of the backbone itself, the size of the solubilizing groups, the orientation of the individual monomer units, the distribution of the stabilizing groups along the backbone, and the match of the dielectric constants and dipole moments of the solubilizing groups and the solvent. Nevertheless, general strategies have been developed. For example, if the rigid-rod or segmented rigid-rod polymers are to be synthesized in polar solvents, the pendant solubilizing groups of the polymer and the monomer starting material will be a group that is soluble in polar solvents. Similarly, if the rigid-rod or segmented rigid-rod polymers are to be synthesized in non-polar solvents, the pendant solubilizing group on the rigid-rod polymer backbone and the monomer starting material will be a group that is soluble in non-polar solvents.

Solubilizing groups which can be used include, but are not limited to, alkyl, aryl, alkaryl, aralkyl, alkyl amide, aryl amide, alkyl thioether, aryl thioether, alkyl ketone, aryl ketone, alkoxy, aryloxy, benzoyl, cyano, fluorine, heteroaryl, phenoxybenzoyl, sulfone, ester, imide, imine, alcohol, amine, and aldehyde. These solubilizing groups may be unsubstituted or substituted as described below. Other organic groups providing solubility in particular solvents can also be used as solubilizing groups. In some embodiments adjacent solubilizing groups may be bridging.

Additional pendant solubilizing side groups include alkylester, arylester, alkylamide and arylamide acetyl, carbomethoxy, formyl, phenoxy, phenoxybenzoyl, and phenyl. Further solubilizing side groups may be chosen from —F, —CN, —CHO, —COR, —CR=NR', —OR, —SR, —SO$_2$R, —OCOR, —CO$_2$R, —NRR', —N=CRR', —NR-COR',—CONRR', and R, where R and R' are each selected independently from the group consisting of H, alkyl, substituted alkyl, aryl, substituted aryl, heteroaryl and substituted heteroaryl.

Unless otherwise specifically defined, alkyl refers to a linear, branched or cyclic alkyl group having from 1 to about 9 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. Linear and branched alkyl group can be saturated or unsaturated and substituted or unsubstituted. A cyclic group is saturated and can be substituted or unsubstituted.

Unless otherwise specifically defined, aryl refers to an unsaturated ring structure, substituted or unsubstituted, that includes only carbon as ring atoms, including, for example, phenyl, naphthyl, biphenyl, 4-phenoxyphenyl and 4-fluorophenyl.

Unless otherwise specifically defined, heteroaryl refers to an unsaturated ring structure, substituted or unsubstituted, that has carbon atoms and one or more heteroatoms, including oxygen, nitrogen and/or sulfur, as ring atoms, for example, pyridine, furan, quinoline, and their derivatives.

Unless otherwise specifically defined, heterocyclic refers to a saturated ring structure, substituted or unsubstituted, that has carbon atoms and one or more heteroatoms, including oxygen, nitrogen and/or sulfur, as ring atoms, for example, piperidine, morpholine, piperazine, and their derivatives.

Unless otherwise specifically defined, "alcohol" refers to the general formula alkyl-OH or aryl-OH.

Unless otherwise specifically defined, "ketone" refers to the general formula —COR including, for example, acetyl, propionyl, t-butylcarbonyl, phenylcarbonyl (benzoyl), phenoxyphenylcarbonyl, 1-naphthylcarbonyl, and 2-fluorophenylcarbonyl.

Unless otherwise specifically defined, "amine" refers to the general formula —NRR' including, for example, amino, dimethylamino, methylamino, methylphenylamino and phenylamino.

Unless otherwise specifically defined, "imine" refers to the general formula —N=CRR' including, for example, dimethyl imino (R and R' are methyl), methyl imino (R is H, R' is methyl) and phenyl imino (R is H, R' is phenyl) and the formula —CR=NR' including, for example, phenyl-N-methylimino, methyl-N-methylimino and phenyl-N-phenylimino Unless otherwise specifically defined, "amide" refers to the general formula —CONRR' including, for example, N,N-dimethylaminocarbonyl, N-butylaminocarbonyl, N-phenylaminocarbonyl, N,N-diphenylaminocarbonyl and N-phenyl-N-methylaminocarbonyl and to the general formula —NRCOR' including, for example, N-acetylamino, N-acetylmethylamino, N-benzoylamino and N-benzoylmethylamino.

Unless otherwise specifically defined, "ester" refers to the general formula —$CO_2R$ including, for example, methoxycarbonyl, benzoyloxycarbonyl, phenoxycarbonyl, naphthyloxycarbonyl and ethylcarboxy and the formula —OCOR including, for example, phenylcarboxy, 4-fluorophenylcarboxy and 2-ethylphenylcarboxy.

Unless otherwise specifically defined, "thioether" refers to the general formula —SR including, for example, thiomethyl, thiobutyl and thiophenyl.

Unless otherwise specifically defined, "sulfonyl" refers to the general formula —$SO_2R$ including, for example, methylsulfonyl, ethylsulfonyl, phenylsulfonyl and tolylsulfonyl.

Unless otherwise specifically defined, "alkoxy" refers to the general formula —O-alkyl including, for example, methoxy, ethoxy, 2-methoxyethoxy, t-butoxy. Unless otherwise specifically defined, "aryloxy" refers to the general formula —O-aryl including, for example, phenoxy, naphthoxy, phenylphenoxy, 4-methylphenoxy.

Unless otherwise specifically defined, R and R' are each independently selected from hydrogen, alkyl, substituted alkyl, heteroalkyl, aryl, substituted aryl, heteroaryl and substituted heteroaryl. Substituent groups useful in the invention are those groups that do not deleteriously affect the desired properties of the inventive compound. Substituent groups that do not deleteriously affect the desired properties of the inventive compound include, for example, alkoxy, alkyl, halogen, —CN, —NCS, azido, amide, amine, hydroxy, sulfonamide and lower alcohol.

The rigid backbone polymers described above could be used in various "forms" in the subject orthodontic invention. In one embodiment the polymers might be used alone as neat resins. In this embodiment, variations of the rigid-rod, segmented rigid-rod or semi-rigid backbone and the solubilizing groups may be desirable to achieve preferred balances of properties.

In another embodiment, rigid backbone polymers can be mixed with any or all of additives, filler materials, plasticizers and reinforcing agents. The resulting compounds have properties that can be tailored to the desired end use. It should be noted that filler materials are added to a polymer matrix predominately to improve wear, alter color or reduce friction of the resulting material. Strength enhancement, while possible, is generally limited with filler material additions. Reinforcing agents such as glass fibers or carbon fibers are added primarily to improve strength properties of the resulting material, sometimes by two or three times the unreinforced strength. Either chopped or continuous reinforcing fibers can be used. The improvement in properties generally increases with the aspect ratio of the fibers. However, reinforcing fibers have several disadvantages, particularly for the inventive orthodontic application. Desirable isotropic properties are lost when using continuous reinforcing fibers. If manipulation of orthodontic components is necessary, such as arch wire adjustments or forming of springs, loops or other desirable shapes, fibers may shift from a uniform, homogeneous distribution, deteriorating mechanical properties. In some inventive variations an orthodontic component consists essentially of a rigid backbone polymer and no more than 5% by weight of a reinforcing agent. As used herein, "an orthodontic component consisting essentially of a rigid backbone polymer and no more than 5% by weight of a reinforcing agent" means that the orthodontic component contains no more than 5% by weight of materials intended primarily to increase the mechanical properties of the polymer.

In a further embodiment, at least one rigid backbone polymer can be used as an effective, molecular reinforcing component in other engineering thermoplastics. For example, a polyphenylene polymer could be blended with other engineering thermoplastics, such as polycarbonate. Blending results in a physical mixing of two distinct polymer chains, for example a rigid-rod polymer chain and a non-rigid-rod polymer chain such as polycarbonate. Blending and polymer blends are intended to encompass all methods of achieving such physical mixing including, for example, coreaction of different monomers to form blended homopolymers. Such polymer blends can yield desirable properties with even small percentages of the polyphenylene polymer. In blends, the combination of the rigid backbone polymer with one or more flexible non-rigid backbone thermoplastic produces what is sometimes referred to as a molecular composite, wherein the rigid backbone molecules are analogous to fibers in a conventional fiber-reinforced composite. However, since molecular composites contain no fibers, they can be fabricated much more easily than fiber-reinforced composites and should be more amenable to forming in an orthodontic clinical setting.

Molecular composites present problems due to the limited solubility and fusibility of the rigid-rod structures and phase separation (in blends) from the more flexible non-rigid backbone polymer. However, the literature teaches that use of the solubilizing groups and/or non-parallel meta-phenylene backbone structures described above alleviates the solubilizing and fusibility problems by somewhat disrupting the regular paraphenylene structure. To address the problem of phase separation, U.S. Pat. No. 5,869,592, the contents of which are incorporated by reference herein, describes the addition of reactive side groups to the phenylene macromonomers that chemically bind the rigid-rod structure to the flexible polymer and help insure maintenance of a uniform distribution of the rigid and flexible units, i.e. a uniform blend is maintained and phase separation is avoided. Such reactive side groups can be defined as compatibilizing side groups.

If many crosslinks are made between the rigid-rod polymer and the flexible polymer the resulting highly crosslinked structure will likely resemble a thermoset and should be processed accordingly. At the other extreme, if only a few reactive side groups per rigid-rod polymer chain are available to form crosslinks, a thermoplastic structure resembling a graft copolymer results. A non-limiting list of flexible polymers that can incorporate a rigid backbone polymer includes polyacetal, polyamide, polyimide, polyester and polycarbonate.

A molecular composite can also be formed by co-polymerization of a rigid-rod and non-rigid-rod polymer units. In co-polymerization the rigid-rod and non-rigid-rod polymer units are chemically bound. The rigid-rod molecules are analogous to fibers in fiber reinforced composites. However, since molecular composites contain no fibers, they can be fabricated much more easily than fiber-polymer composites and should be more amenable to forming in an orthodontic clinical setting. The rigid-rod and non-rigid-rod monomer units can have various molecular architectures including, for example, a crosslinked polymer, a graft co-polymer or a semi-interpenetrating network.

In other embodiments, the rigid backbone polymer finds use as a post-polymerization additive. As a post-polymerization additive a rigid backbone polymer may be used in compounding, blending, alloying, or otherwise mixing with preformed polymers, preformed blends, alloys or mixtures of polymers. In these cases the solubilizing side groups and/or reactive side groups help make the rigid-rod polymer compatible with the non rigid-rod polymer to be reinforced. Such compounding, blending, alloying, etc. may be done by solution methods, melt processing, milling, calendering, grinding or other physical or mechanical methods, or by a combination of such methods.

Some properties of the above rigid backbone polymers are listed in Table 2. It should be noted that the properties listed in Table 2 are for neat polymers. As used herein, a neat polymer consists of a polymer resin with essentially no other materials. A neat resin does not include, for example an additive, a filler, another polymer resin, a plasticizer or a reinforcing agent. Naturally, rigid backbone polymers when combined with fillers and/or reinforcing agents can provide even greater mechanical properties.

TABLE 2

| Property | rigid-rod polymer | semi-rigid-rod polymer |
| --- | --- | --- |
| density (g/cm$^3$) | 1.21 | 1.23 |
| refractive index | 1.71 | 1.66–1.70 |
| glass transition temperature (° C.) | 160 | 165 |
| tensile strength (MPa) | 207 | 207 |
| tensile modulus (GPa) | 10.3 | 8.3 |
| flexural strength (MPa) | 310 | 310 |
| flexural modulus (GPa) | 9.7 | 8.3 |
| elastic deformation | 32 | 37 |
| hardness, Rockwell B | 89 | 80 |
| hardness, pencil | ≧9H | 7h |

As can be seen from Table 2, the rigid backbone polymer materials unexpectedly have suitable properties in the unreinforced condition for clinical movement of teeth. In fact, according to calculations for stiffness, in orthodontic applications a 0.53 mm×0.69 mm (0.021 inch×0.027 inch) unreinforced Parmax® 1200 wire would function like a 0.41 mm (0.016 inch) diameter beta titanium wire; a 0.56 mm (0.022 inch) diameter unreinforced Parmax® 1200 wire would function like a 0.36 mm (0.014 inch) diameter beta titanium wire and a 0.48 mm (0.019 inch) diameter unreinforced Parmax® 1200 wire would function like a 0.41 mm (0.016 inch) diameter nickel-titanium wire. In some inventive variations an orthodontic component can be prepared consisting essentially of a rigid backbone polymer. As used herein, "an orthodontic component consisting essentially of a rigid backbone polymer" means that the orthodontic component does not contain any material in the polymer matrix that would affect the desirable properties of the neat rigid backbone polymer.

Figure 3:
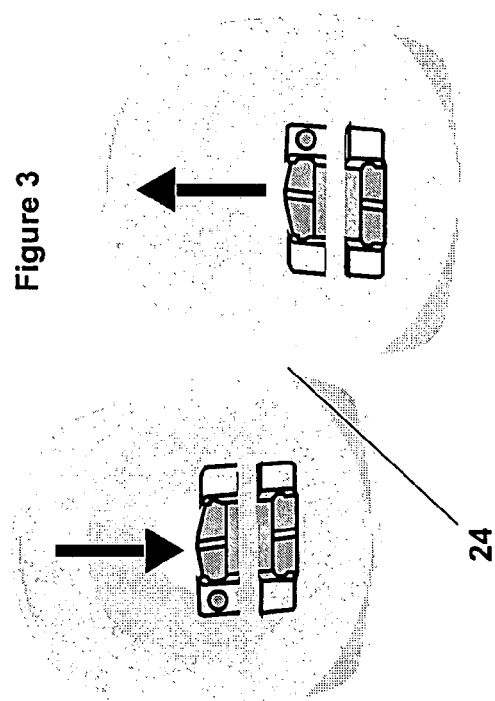
FIG. 3 is a schematic illustration of a portion of an orthodontic appliance showing an elastically deformed force delivery component releasing energy to a pair of bonded brackets.
Figure 1:
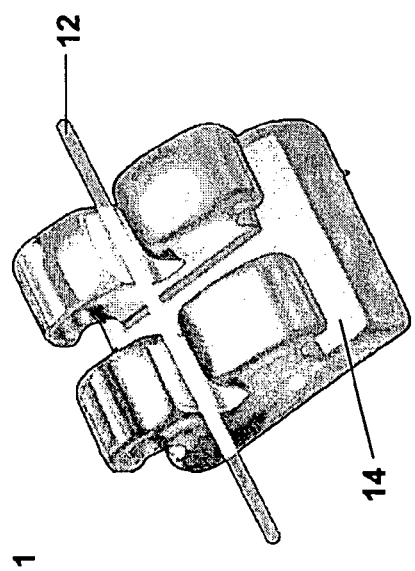
FIG. 1 is a perspective view of one embodiment of an inventive force delivery component engaged within slots of an inventive bracket.

The advantageous combination of high strength, high modulus and high elastic deformation (flexural strength/flexural modulus) properties of rigid backbone polymers make them desirable for use as inventive orthodontic force delivery components such as the wires 12, 24 shown in FIGS. 1 and 3 respectively.

Some rigid backbone polymers have completely amorphous structures so that their strength related properties are isotropic. No orientation of this type of polymer is necessary to achieve desired strength properties. Rigid backbone polymer isotropy is desirable as it eases manufacture of the inventive orthodontic components. Further, the inventive orthodontic components have relatively constant properties in all directions easing use of the inventive components. Naturally, other inventive orthodontic components comprising rigid backbone polymers incorporating a reinforcing agent may exhibit anisotropic strength properties depending on the reinforcing agent if desired for a particular application.

An important property of an orthodontic force delivery component is resistance to creep or minimal stress relaxation. Traditional polymers can exhibit high elastic deformation, however, loads under the yield strength cause permanent deformation over time making them unsuitable for both bracket and wire applications. A surprising property of rigid backbone polymers is their creep resistance and their ability not to deform over time.

Another advantageous property of rigid backbone polymers is hardness. As can be seen from Table 2, rigid backbone polymers can have hardnesses of up to about 80 to about 89 on the Rockwell B scale. These rigid backbone polymer hardness values are among the highest of any thermoplastic polymer material. These hardness properties make rigid backbone polymers highly scratch and abrasion resistant and provide exceptionally good wear characteristics.

Rigid backbone polymers can range from almost transparent to a translucent light yellow in color. As can be seen from Table 2, the refractive index of two exemplary rigid backbone polymers ranges from 1.66 to 1.71, closely matching the 1.66 refractive index of tooth enamel.

Inventive orthodontic components produced from a rigid backbone polymer material have an intrinsically pleasing aesthetic appearance. In some embodiments, a rigid backbone polymer can also be blended with dyes, filler materials or other additives to impart a desired color to the inventive orthodontic component produced therefrom allowing, for example, a close approximation to tooth coloring and great aesthetic acceptance. It should be understood that inventive orthodontic components composed of a rigid backbone polymer can be evenly colored throughout their extent. Thus, the inventive orthodontic components are not susceptible to peeling or wear through of surface coatings.

In another embodiment of the invention a rigid backbone polymer can be molded over an insert to provide a composite orthodontic component. Alternatively, a rigid backbone polymer can be coated over an orthodontic component. The rigid backbone hardness properties make such composite components and coatings more resistant to wear than known coatings.

Rigid backbone polymers are thermoplastic and can be thermally processed by, for example, injection molding, compression molding or extrusion. Typical compression molding conditions are about 300° C. to about 350° C., with pressures of about 0.689 MPa (100 psi) using either polymer powder or pellets. Injection molding is also believed to be a viable thermal processing method for some rigid backbone polymers. Thus, another aspect of the invention is fabrication of these polymers into a novel orthodontic component or a novel orthodontic component precursor using known thermoplastic polymer thermal processing techniques. As one example, inventive force delivery components 26, 28, 30, 32 having different cross sectional shapes such as shown in FIGS. 4a–4d respectively can be formed by extrusion. In another variation, the thermoplastic nature of rigid backbone polymers allows the creation of variations in cross sectional configuration, e.g., cross sectional size and shape. For example the wire 34 diameter can change along its length as shown in FIG. 5a or the wire 36 can twist along its length as shown in FIG. 6. This feature is desirable since orthodontic biomechanics are more dependent on appliance geometry than material mechanical properties, i.e., stiffness and maximum force vary with a power of the component dimension, but only linearly with material mechanical properties. Thus, varying the cross-sectional configuration of an inventive wire along its length allows greater flexibility in design of an orthodontic force system than is presently possible. The efficiency of an orthodontic appliance depends on the magnitude of force produced and its constancy of action during tooth movement. This in turn is dependent in part on having a good fit between the orthodontic components, for example between wire and bracket. Varying the cross section along a wire allows for force control in three dimensions and optimal fit or play between the wire and attachment depending on the individual requirements of a patient.

The thermoplastic nature of rigid backbone polymers further allows secondary thermal forming of orthodontic component precursors or prefabricated orthodontic components. For example, an orthodontic precursor comprising a straight section of extruded rigid backbone polymer can be thermal processed between rolls to provide a shape similar to the wire 26 in FIG. 4a. As another example a novel prefabricated orthodontic component can be thermally formed to modify the component shape and produce inventive orthodontic components with complex shapes such as the auxiliary 44 shown in FIG. 5b and the ligating spring 40 shown in FIG. 11. Such forming procedures can allow dental personnel to form or modify the inventive orthodontic components for subsequent placement by an orthodontist.

Figure 8:
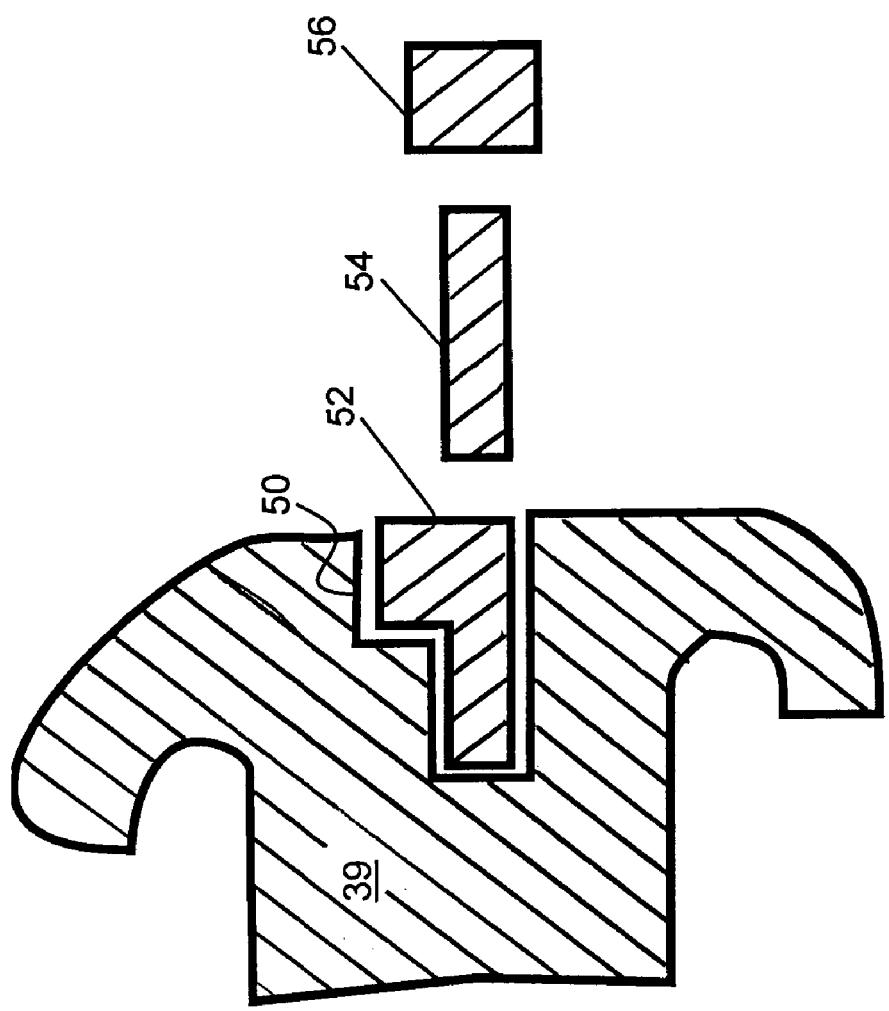
FIG. 8 is a cross sectional representation illustrating three inventive wire embodiments each having shapes configured to register within a mating bracket slot.
Figure 7:
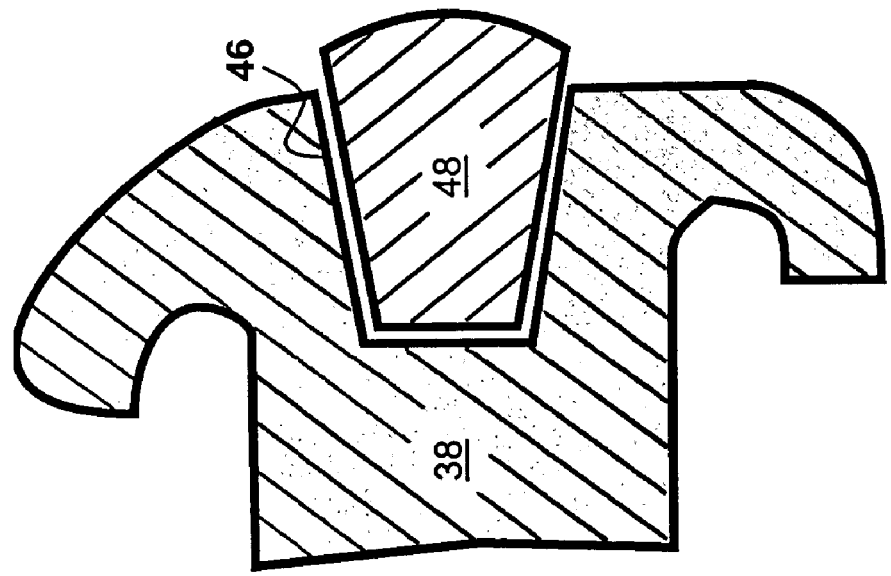
FIG. 7 is a cross sectional representation of one embodiment of an inventive wire having a shape configured to register within a mating bracket slot.
Figure 12A:
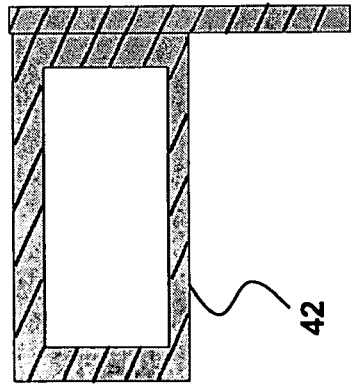
FIG. 12a is a cross sectional representation of one embodiment of an inventive tube with an attached hook.
Figure 12B:
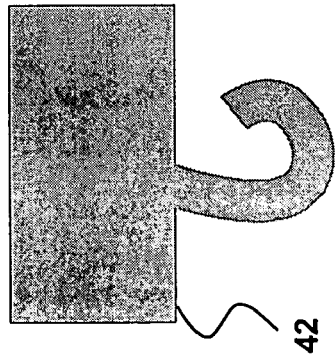

Novel orthodontic components such as a bracket (38, 39 in FIGS. 7 and 8 respectively) or tube (42 in FIG. 12a) comprising a rigid backbone polymer can be formed by, for example, compression molding or injection molding. The inventive brackets can include many novel slot configurations, for example the embodiments shown in FIGS. 7 and 8. The slot 46 configuration in FIG. 7 allows interengagement with an inventive wire 48 having a keystone shape. Interengagement may be maintained with wires of different thickness, e.g. base to opposing arcuate crown. The slot 50 configuration in FIG. 8 allows interengagement with inventive wires 52, 54 or 56 having different shapes. Multiple wires, for example wire 54 and wire 56, can also be used together in slot 50. The invention also envisions interengagement of other orthodontic components, for example, ligation caps or ligation mechanisms.

Interengagement of the slot, for example 46, and wire, for example 48, provides a good fit between the bracket slot and wire, thereby decreasing play between the bracket slot and wire. As used herein, a good fit between the wire and bracket means the wire, when inserted into the bracket, is restricted to a rotational movement around the wire longitudinal axis of no more than about plus or minus 5 degrees. Further, interengagement of the wire and bracket slot allows the same bracket to be a good fit with wires of different sizes and configurations, for example wire 56 or wire 54 in slot 50. In use, a bracket is attached to a tooth and a first wire having a first cross section is interengaged to provide a first desired orthodontic force system. Subsequently, the first wire can be removed and a second wire having a cross section different from the first cross section is interengaged in the same bracket to provide a different desired orthodontic force system. Similarly, subsequent wires of diffent cross sections could be employed. Since each wire will interengage with the same bracket slot to provide a good fit, control of the orthodontic force system is not lost when the wire is changed. A conventional bracket can, at best, provide a good fit with only a single conventional wire size. Thus, this aspect of the invention functions to provide greater control of the orthodontic force system than is presently possible using conventional wires and brackets.

Figure 9:
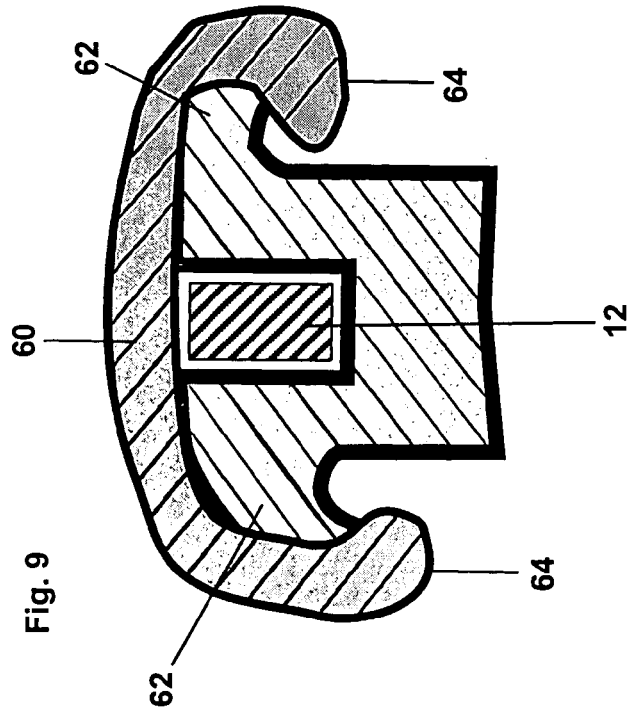
FIG. 9 is a cross sectional representation of one embodiment of the invention illustrating an inventive retaining cap securing an inventive wire within a bracket slot.

Orthodontic components such as restraining cap 60 shown in FIG. 9 comprising a rigid backbone polymer can be formed by, for example, extrusion, compression molding or injection molding. The novel restraining cap 60 is configured to clamp around the tie wings 62 of a bracket and secure a force delivery component 12 within the bracket slot. The configuration of the restraining cap 60 allows the cap to slide over the tie wings 62. Alternatively, the restraining cap 60 is sufficiently resilient to elastically expand as it is pushed over the bracket, and contract when the locking arm 64 moves under the tie wing 62, securing the restraining cap 60 to the bracket and maintaining the force delivery component within the bracket slot.

The rigid backbone polymer materials can be machined and finished on standard equipment to form inventive orthodontic components. Typically, rigid backbone polymer materials can be machined in a manner similar to aluminum with a resulting surface finish also similar to aluminum. Tools and techniques designed for plastics or laminates can also successfully be used with rigid backbone polymer materials. It should be noted that most metalworking fluids can be used with rigid backbone polymers including mineral oils that would dissolve or attack other polymers.

Figure 10:
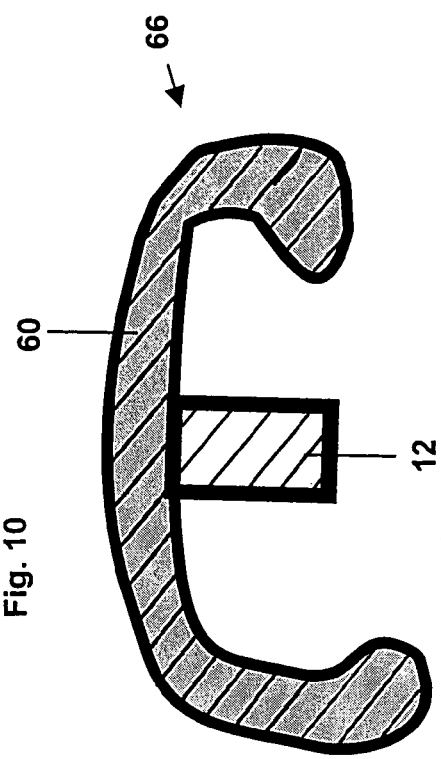
FIG. 10 is a cross sectional representation of one embodiment of the invention illustrating an inventive integral retaining cap and wire.

Advantageously, inventive orthodontic components can be bonded to each other using heat or adhesives, for example a dimethacrylate based adhesive. Orthodontic components comprised of rigid backbone polymers are believed to be bondable to a tooth enamel surface using commercially available orthodontic adhesives such as TRANSBOND available from 3M-Unitek. Some form of mechanical retention, i.e. undercuts or roughening, designed into the orthodontic components would be advantageous to achieve bonding between the components and tooth enamel. Bondability of the inventive components is desirable to allow flexibility in design of the orthodontic force system. A restraining cap 60 can be bonded at selected locations along the length of a wire 12 to form an integral restraining cap and wire 66 as shown in FIG. 10.

It should be understood that the following examples are included for purposes of illustration so that the invention may be more readily understood and are in no way intended to limit the scope of the invention unless otherwise specifically indicated.

EXAMPLE 1

Properties of Rigid Backbone Brackets

Figure 14:
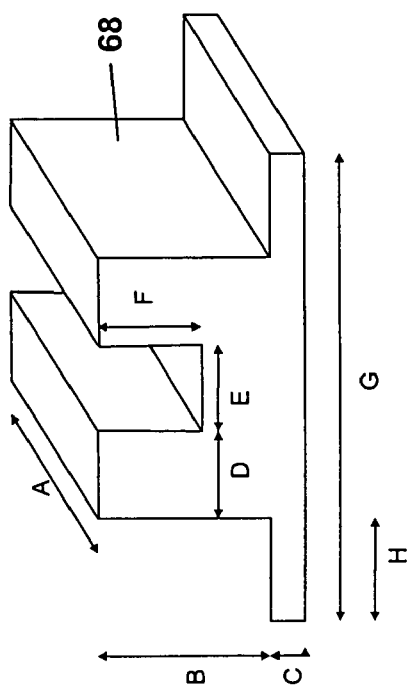
FIG. 14 is a perspective view of a test bracket.

Orthodontic brackets 68 as shown in FIG. 14 were machined from a compression molded plaque of random copolymer of benzoyl appended 1,4-phenylene (15 mol % of the repeat units) and 1,3-phenylene (85 mol % of the repeat units) (available as Parmax® 1200 from Mississippi Polymer Technologies, Inc.). The orthodontic brackets 68 had four different bracket wall thicknesses; 0.51 mm, 0.99 mm, 1.5 mm and 2.0 mm (0.020, 0.039, 0.059 and 0.079 inch). Polycarbonate brackets with identical design were used as a control. A 0.53 mm×0.64 mm (0.021×0.025 inch) stainless orthodontic wire the bracket occurred. Moments were continuously monitored with a torque gauge. As shown in FIGS. 15 and 16, the rigid backbone (Parmax® 1200) brackets 68 showed a significant improvement in both stiffness and the maximum moment at failure as compared to the polycarbonate bracket.

EXAMPLE 2

Properties of Rigid Backbone Force Delivery Components

Orthodontic wires were fabricated from a compression molded plaque of poly-1,4-(benzoylphenylene) (available as Parmax® 1000 from Mississippi Polymer Technologies, Inc.) and a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.) by machining to a dimension of 0.53 mm×0.64 mm (0.021 inch×0.025 inch). A 5 millimeter wire span length simulating an intra-oral inter-bracket distance was loaded using a cantilever test. A torque gauge recorded the moment at the attached end of the wire. Polycarbonate wires were used as a control. The test data clearly demonstrates the ability of the rigid backbone (Parmax® 1000 and Parmax®1200) wires to deliver sufficient force, low force-deflection rates, and a large elastic deflection needed for orthodontic tooth movement (FIGS. 17 and 18). The polycarbonate wires by comparison delivered forces that were too low to produce desired tooth movement.

EXAMPLE 3

Permanent Deformation of Rigid Backbone Orthodontic Wires

A straight section of orthodontic wire with dimensions of 0.021 inches×0.025 inches was cut from a compression molded plaque of poly-1,4-(benzoylphenylene), (available as Parmax® 1000 from Mississippi Polymer Technologies, Inc.) using a slow speed diamond saw. The wire was positioned into two misaligned orthodontic brackets. The edge-to-edge and center-to-center interbracket distances were 7 mm and 11 mm, respectively. The brackets were misaligned 3 mm in the apical-occlusal direction. There was no rotation in the brackets. The wire was removed after 1, 2 and 3 hour intervals. The apical-occlusal permanent deformations within the 7 mm interbracket region at the three time periods were 0.0 mm, 0.24 mm and 0.14 mm, respectively. There was no indentation of the rigid backbone (Parmax® 1000) wire, indicating that the wire had sufficient hardness. There was no discoloration or white regions at critical sections of the rigid backbone wire indicating no failure of the wire had occurred.

EXAMPLE 4

Water Immersion

A free-end cantilever test was used to evaluate flexural properties before and after water immersion. Materials tested were poly-1,4-(benzoylphenylene) (available as Parmax® 1000 from Mississippi Polymer Technologies, Inc.) and a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.). Polycarbonate (Tuffak™ available from Atohaas) was used as a control.

Two samples of each material were prepared with dimensions of 0.53 mm×0.64 mm×50.0 mm (width×thickness×length) to simulate an orthodontic wire. Samples were conditioned in an oven for 24 hours at 50° C. and cooled in a desiccator. Following conditioning, one sample of each material was placed in a capped vial filled with deionized water. The vials were placed in a water bath maintained at 37° C. The second 50 mm long sample of each material was maintained in a desiccator. Samples were removed from the desiccator at 5 days and from the water bath (and towel dried) at 5 days, 30 days and 365 days and cut to lengths of 15 mm to accommodate a test span length of 5 mm. A free-end cantilever test was used to measure flexural rigidity, moment at yield and displacement at yield. These properties are listed in Table 3.

TABLE 3

|  | Parmax ® 1000 | Parmax ® 1200 | Polycarbonate |
| --- | --- | --- | --- |
| Flexural Rigidity (g-mm/degree) | | | |
| Before Immersion | 41 | 36 | 13 |
| 5 days | 42 | 38 | 16 |
| 30 days | 51 | 53 | 22 |
| 365 days | 62 | 43 | 18 |
| Moment at Yield (g-mm) | | | |
| Before Immersion | 950 | 933 | 300 |
| 5 days | 883 | 858 | 325 |
| 30 days | 708 | 650 | 279 |
| 365 days | 942 | 875 | 325 |
| Displacement at Yield (degrees) | | | |
| Before Immersion | 28 | 32 | 33 |
| 5 days | 28 | 28 | 28 |
| 30 days | 14 | 14 | 13 |
| 365 days | 17 | 23 | 28 |

After 365 days of water immersion the Parmax® 1200 sample showed no change in flexural rigidity or moment at yield but did exhibit a possible decrease in displacement at yield. After 365 days of water immersion the Parmax® 1000 sample showed no change in moment at yield but did exhibit a possible increase in flexural rigidity and decrease in displacement at yield. The inventors believe that the changes could be due to experimental error and even if real that the changes are clinically insignificant. As can be seen from the results of Table 3, the rigid backbone wires have surprisingly improved mechanical properties, both initially and after extended water immersion, when compared to wires made of known polymer materials.

EXAMPLE 5

Color Stability

A modified version of ANSI/ADA Specification No. 12 was used to compare the color stability of polyphenylene polymers to standard polymers used in orthodontics. Samples tested were poly-1,4-(benzoylphenylene) (available as Parmax® 1000 from Mississippi Polymer Technologies, Inc.); a random copolymer of benzoyl appended 1,4- phenylene (15 mol % of the repeat units) and 1,3-phenylene (85 mol % of the repeat units) (available as Parmax® 1200 from Mississippi Polymer Technologies, Inc.); polycarbonate (Tuffak™, available from Atohaas); and commercial orthodontic polyurethane "O-rings" (SoloTie-Clear™, available from Class One Orthodontics). Two samples of each material were made with dimensions of 0.53 mm×2.28 mm×15 mm to simulate the thickness of an orthodontic wire, except for the "O-rings" which were used as-manufactured. One control sample of each polymer material was wrapped in aluminum foil and placed in a box to prevent exposure to light. A second sample for each polymer material was exposed to a combination of white light from a standard 60-watt, 120-volt incandescent bulb and a black light (Black-Ray Lamp model UVL-56, long wave UV-366 nm, 115 volts, 60 Hz, 0.16 amps, UVP, Inc., San Gabriel, Calif.). Samples were placed on an aluminum plate, positioned 17.8 cm away from the light source, and exposed for 24 hours. Following exposure all samples were visually compared to control samples. There were no visually detectable differences between the exposed rigid backbone polymers (Parmax® 1000 and Parmax® 1200) and their controls; or the polycarbonate sample and its control. The exposed polyurethane sample (about 10 O-rings evaluated as a unit) had a slight brown/yellow tint relative to their unexposed controls. As can be seen from the results, the rigid backbone samples have improved color stability when compared to some known orthodontic polymer materials.

EXAMPLE 6

Staining Resistance

Resistance to common staining agents was evaluated. Samples tested were poly-1,4-(benzoylphenylene) (available as Parmax® 1000 from Mississippi Polymer Technologies, Inc.); a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.); polycarbonate (Tuffak™, available from Atohaas); and commercial orthodontic polyurethane "O-rings" (SoloTie-Clear™, available from Class One Orthodontics). Four samples of each material were made with dimensions of 0.53 mm×2.28 mm×15 mm to simulate the thickness of an orthodontic wire except for the "O-rings" which were used as manufactured.

One sample for each polymer material was exposed to each of the following three coloring agents: mustard, tea and red wine. To prepare the coloring agents, the mustard was mixed with deionized water at a ratio of 1:5, one black tea bag was added to 250 mL of hot water, and the red wine was used at full strength. One sample for each polymer material was exposed to deionized water and used as a control. Samples were immersed in the coloring agents for 24 hours and maintained at 37° C. Following exposure samples were blotted dry and visually compared to the deionized water controls by three examiners. Relative to the controls the samples were scored as no different (−−), slightly different (+), clearly stained (++), or dark staining (+++). Results of the staining comparison are shown in Table 3.

TABLE 4

|  | Mustard | Tea | Red Wine |
| --- | --- | --- | --- |
| Parmax ® 1000 | −− | −− | −− |
| Parmax ® 1200 | + | −− | −− |

TABLE 4-continued

|  | Mustard | Tea | Red Wine |
| --- | --- | --- | --- |
| Polycarbonate | + | ++ | +++ |
| Polyurethane | +++ | +++ | +++ |

As can be seen from the results of Table 4, the rigid backbone samples have improved resistance to staining from contact with common food items when compared to known orthodontic polymer materials.

EXAMPLE 7

Creep or Stress Relaxation of Rigid Backbone Orthodontic Wires

Parmax® 1200 and polycarbonate wires were placed in two brackets with non-aligned slots of 3 mm and an interbracket distance of 7 mm. Instantaneous measurement showed negligible permanent deformation of both wires. The load was maintained for 24 hours and permanent deformation measured. The Parmax® wire had negligible deformation (0.3 mm) and the polycarbonate wire showed 1.2 mm deformation, which was 40% of the total deflection.

EXAMPLE 8

Extruded Rigid Backbone Orthodontic Wires

Five sets of 1.0 mm (0.040 inch) diameter round orthodontic wires were extruded. Uniform round cross sections were maintained to a tolerance under 10%. The extruded wires were neat Parmax® 1200, neat Parmax® 1000 and one set of wires comprising Parmax® with a plasticizer. The wires exhibited good aesthetics possessing translucency with a slight yellow tint.

Figure 19:
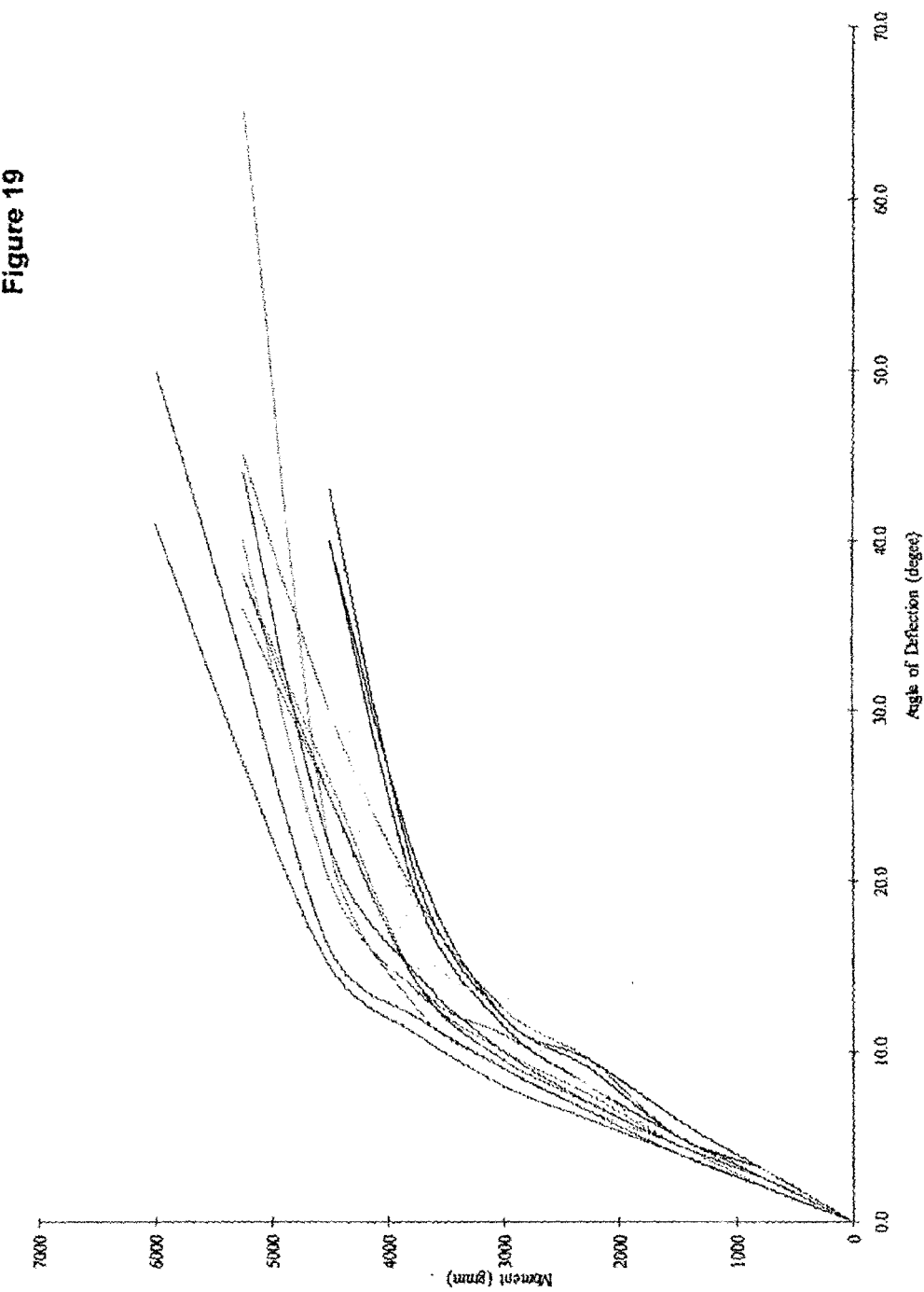
FIG. 19 is a graph showing load-deflection curves for some inventive orthodontic components.

A cantilever test was performed on 5 mm long specimens applying 750 g-mm load increments with a torque gauge until failure. The graph in FIG. 19 shows adequate stiffness, approximately 200 g-mm/degree, for demanding orthodontic tooth movement. The maximum moment (moment at yield) was within a range of 3000–4500 g-mm allowing for the application of heavier orthodontic forces if required. This data illustrates that a Parmax® wire can be scaled down in size and still be capable of delivering sufficiently high forces for efficient tooth movement if smaller attachments are used.

FIG. 19 also shows the remarkable high elastic deformation of the Parmax® wires, which was between 10° and 15°. The extruded wires demonstrated good ductility with deflection in the plastic range as large as 50°. Ductility is important to prevent wire breakage under clinical conditions.

EXAMPLE 9

Forming of Rigid Backbone Orthodontic Wires

Orthodontic wires were manipulated by hand to form selective curves and bends that would be necessary to form various orthodontic appliance designs. The wires were a 1.07 mm diameter extrusion of a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.). The necessary conditions for forming the wires were determined by heating the samples to various combinations of temperatures and times in a laboratory oven. Samples 70 mm in length were heated at temperatures between 180° C. and 200° C. for 5 to 20 minutes. Samples heated to 195° C. for at least 15 minutes, or advantageously at 200° C. for 10 minutes or more, were sufficiently soft to be readily formed into desired orthodontic configurations. The forming had to be done quickly before the samples cooled to their unheated state.

EXAMPLE 10

Forming of Rigid Backbone Orthodontic Archwires

Figure 20:
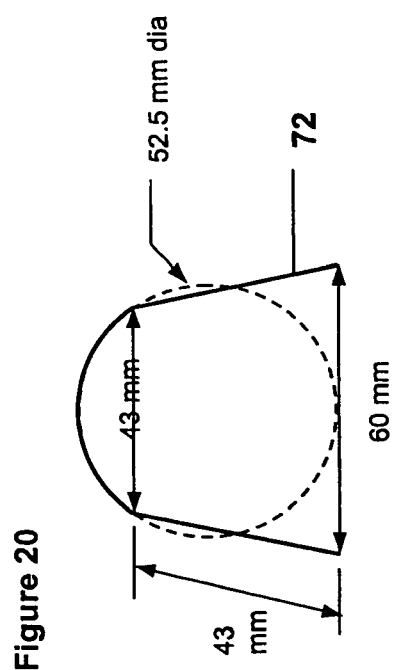
FIG. 20 schematically illustrates an inventive archwire formed by heat processing.

Using a custom-made two-part aluminum mold an orthodontic archwire 72, as shown schematically in FIG. 20, was formed from a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.). The shape was similar to the upper medium Tru Arch™ (A Company) arch form. To prepare archwire 72 generally straight lengths of the rigid backbone polymer were extruded with a diameter of approximately 1.0 mm. The arch shape was achieved in three stages. First, a straight length of the rigid backbone polymer was heated to 200° C. for 15 minutes, removed from the oven and formed by hand to the approximate shape of the aluminum mold. Next, the precursor wire and mold were heated together at 200° C. for an additional 15 minutes, removed from the oven and the sections of the mold were slid together to form the precursor wire closer to the desired shape. The mold and precursor wire were placed in the 200° C. oven for a final 15 minutes, then allowed to bench cool for one hour before the wire was removed from the mold. Thereafter the wire 72 maintained the desired arch shape.

EXAMPLE 11

Reducing Rigid Backbone Wire Dimension to Fit Orthodontic Brackets.

The cross-sectional dimension of straight lengths of a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.) was reduced from approximately 1 mm (0.040 inch) to 0.53 mm (0.021 inch) to fit into standard orthodontic brackets. This was achieved by clamping the rigid backbone wire and 0.53 mm (0.021 inch) stainless steel spacers between aluminum platens heated to 200° C. The clamps were tightened after each of four successive 15-minute heating periods. The assembly was allowed to bench cool for 20 minutes before the clamps and wire were removed. The inventive wire had two opposing flat faces connected by arcuate sides. This procedure was also applied to the archwire formed in Example 10.

EXAMPLE 12

Clinical Applications of Rigid Backbone Orthodontic Wire

Figure 21A:
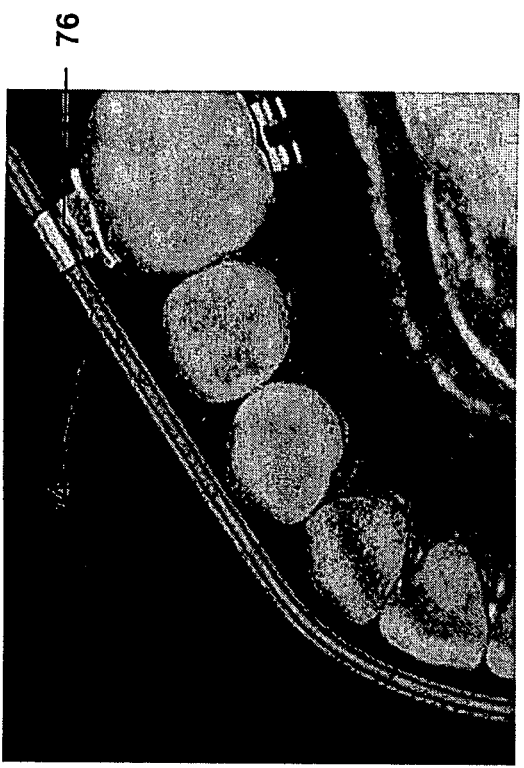
FIGS. 21a, 21b and 21c each illustrate the placement and use of an inventive archwire in an orthodontic appliance installed on a model.
Figure 21C:
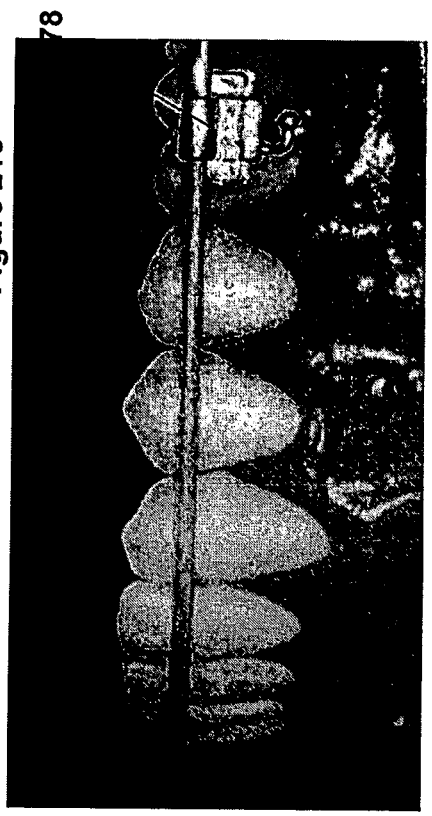
Figure 21B:
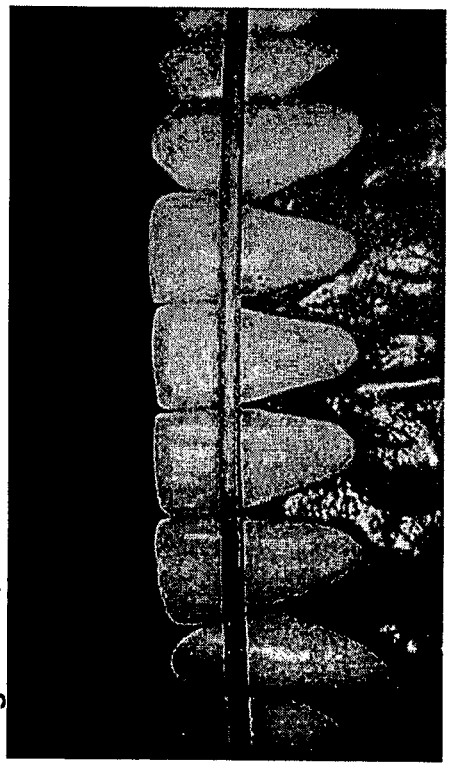

A rigid backbone archwire 74 was inserted into two posterior buccal tubes 76, 78 as anchor units as shown in FIGS. 21a, 21b and 21c. Ligature wires, elastomeric rings or elastic thread could be placed to move anterior teeth in the desired direction. This includes overbite reduction, closing of open bites, tooth alignment or rotation and cross bite correction. Attachments could be placed as needed on the anterior teeth.

Figure 22:
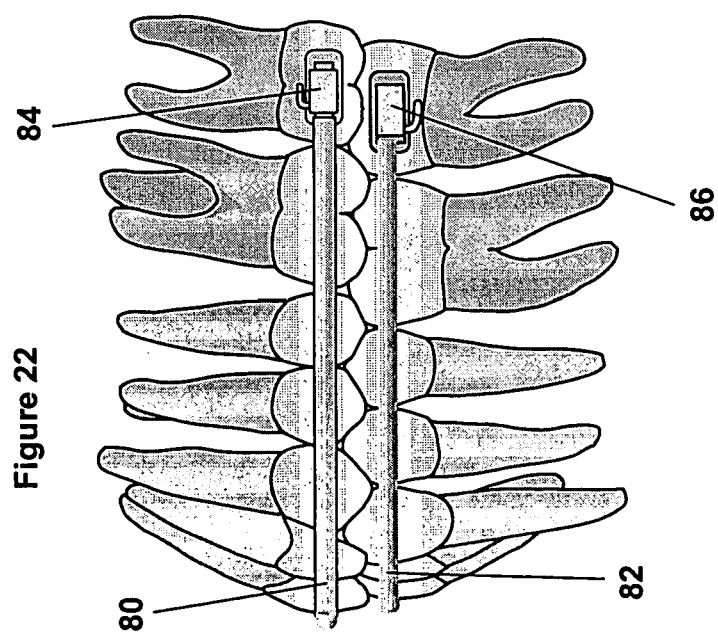
FIG. 22 schematically illustrates placement and use of upper and lower archwires in an orthodontic appliance.

FIG. 22 schematically illustrates upper and lower archwires, 80, 82 respectively, inserted into upper and lower buccal tubes, 84, 86 respectively. Ligature ties can be placed to move any of the teeth anterior to the second molars that have attached tubes.

Figure 23:
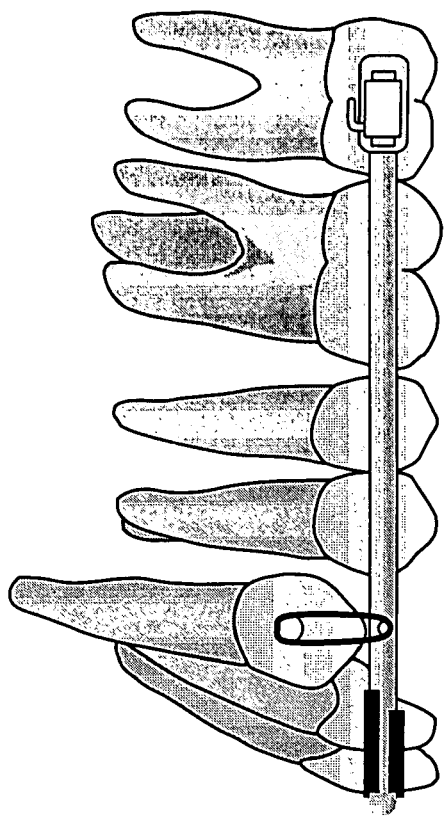
FIG. 23 schematically illustrates use of an inventive archwire as part of an orthodontic appliance before orthodontic correction.
Figure 24:
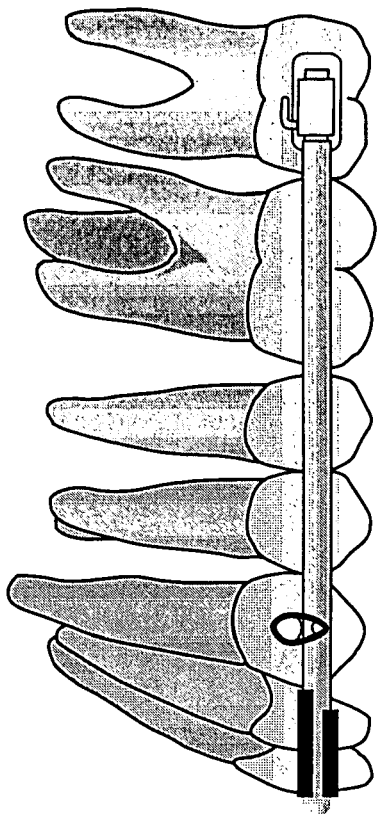
FIG. 24 schematically illustrates use of the inventive archwire of FIG. 23 after orthodontic correction.

FIGS. 23 (before) and 24 (after) schematically illustrate an elastic attached to a rigid backbone polymer archwire to extrude a canine tooth.

Figure 25:
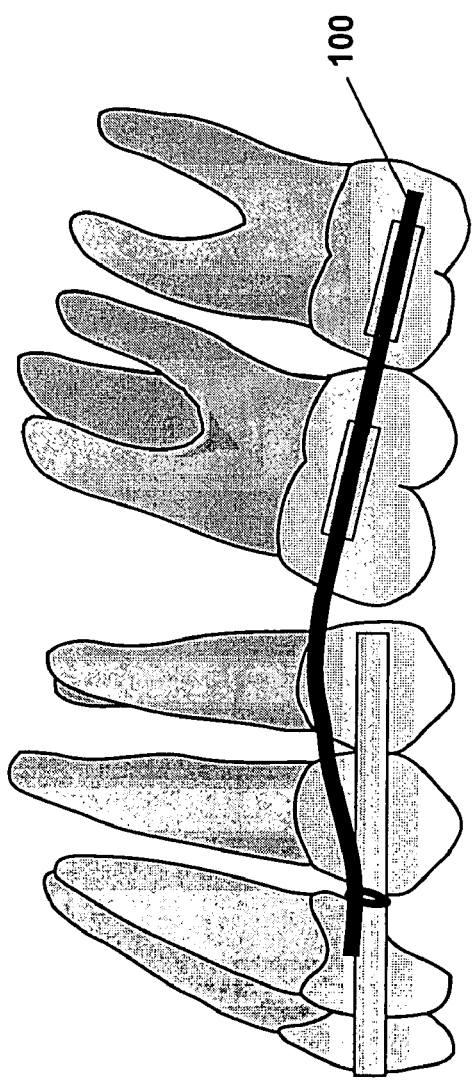
FIG. 25 schematically illustrates use of an inventive force delivery component as part of an orthodontic appliance before orthodontic correction.
Figure 26:
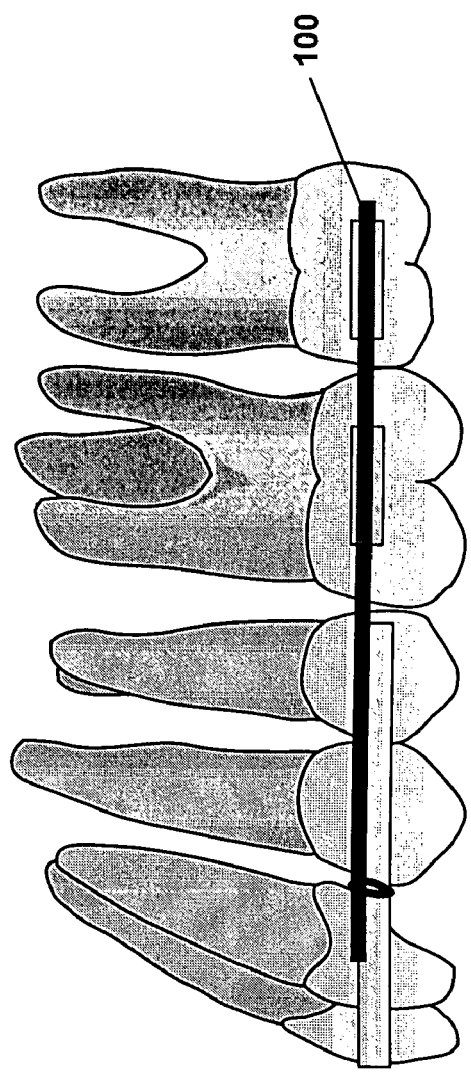
FIG. 26 schematically illustrates use of the inventive force delivery component of FIG. 25 after the orthodontic correction.

FIGS. 25 (before) and 26 (after) schematically illustrate a segmental 1 mm (0.040 inch) diameter rigid backbone polymer wire 100 used to upright a tipped posterior segment. The inventive segmental wire 100 is attached to a rigid esthetic anterior segment made of a fiber-reinforced composite or suitable polymer.

EXAMPLE 13

Clinical Applications of Rigid Backbone Aligners

Figure 27:
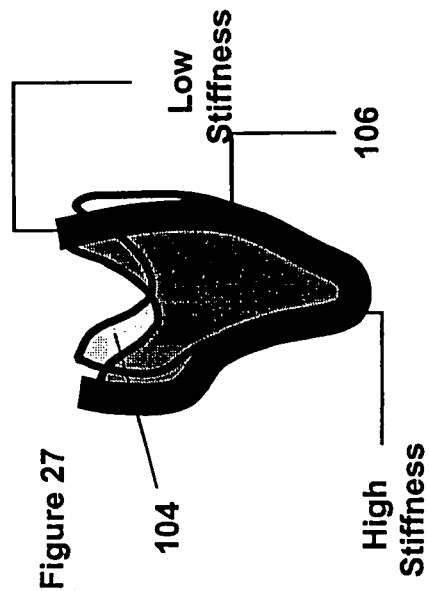
FIG. 27 schematically illustrates a removable orthodontic aligner with varying stiffness at the incisal and gingival portions to effect lingual root movement.

The efficiency of an orthodontic tooth aligner can be enhanced with the use of a rigid backbone polymer component. Current esthetic polymers with lower modulus, yield strength and hardness than a rigid backbone polymer lack the rigidity and shape stability to produce exacting detail in tooth alignment, particularly in the finishing stages of aligner treatment. Rigid backbone polymers with higher mechanical properties would be able to produce more exacting detailed alignment. For example, as shown in FIG. 27 most tooth movement requires varying deflection of points on a tooth. Thus, variation in stiffness by using different materials in a single aligner is desirable. The high stiffness of rigid backbone polymers can be part of such a system. For example, if the inclination of a tooth requires correction wherein the root is moved lingually and the crown is maintained in its approximate initial position, the high stiffness rigid backbone polymer is placed around the incisal-crown portion of the aligner and a low stiffness polymer is placed apically in the gingival-crown region.

Figure 28:
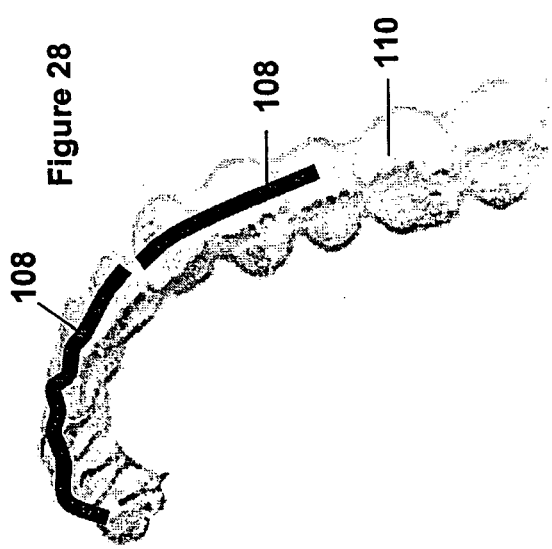
FIG. 28 schematically illustrates an inventive force delivery component incorporated into a removable aligner.

As a further example a rigid backbone polymer wire 108 can be incorporated into an aligner 110 as shown in FIG. 28 to improve tooth movement and anchorage control. In this application a rigid backbone wire is applied to the crowns of the teeth to produce detailed tooth movement. This wire is embedded in a lower stiffness aligner that serves two purposes, to position the rigid backbone wire and to offer the remainder of the arch for anchorage.

EXAMPLE 14

Evaluating the Effect of Time and Temperature on Rigid Backbone Polymer Flexure Properties.

Flexure tests were conducted on 1.17 mm diameter rigid backbone polymer wires to determine if the various time and temperature combinations used in clinical forming affected mechanical properties of the formed component. 50 mm long by 1.17 mm diameter wires of a random copolymer of benzoyl appended 1,4-phenylene (15 mol % of the repeat units) and 1,3-phenylene (85 mol % of the repeat units) (available as Parmax® 1200 from Mississippi Polymer Technologies, Inc.) were heated to 200° C. for periods of 10 to 80 minutes and between 185° C. and 210° C. for 15 minute periods. Each sample was allowed to bench cool and was cut into three 15 mm long samples. The samples were tested as 5 mm cantilevers recording angular deflection and torque. As shown in the tables below there were no significant changes in flexure properties.

TABLE 5 constant temperature (200° C.) for various times

| Time (minutes) | Flexure rigidity (g * mm/degrees) | Displacement at Yield (degrees) | Moment at Yield (g * mm) |
|---|---|---|---|
| control | 383 | 8.2 | 3000 |
| 10 | 363 | 8.5 | 3000 |
| 20 | 351 | 8.7 | 3000 |
| 30 | 343 | 8.8 | 3000 |
| 40 | 356 | 8.5 | 3000 |
| 50 | 357 | 11.3 | 3750 |
| 60 | 374 | 8.3 | 3000 |
| 70 | 368 | 8.3 | 3000 |
| 80 | 348 | 8.8 | 3000 |

TABLE 6 constant time (15 minutes) for various temperatures

| Temperature (° C.) | Flexure rigidity (g * mm/degrees) | Displacement at Yield (degrees) | Moment at Yield(g * mm) |
|---|---|---|---|
| control | 396 | 8.2 | 3000 |
| 185 | 352 | 8.2 | 3000 |
| 190 | 383 | 8.2 | 3000 |
| 195 | 365 | 8.5 | 3000 |
| 200 | 351 | 8.7 | 3000 |
| 205 | 390 | 8.0 | 3000 |
| 210 | 396 | 8.0 | 3000 |

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. An orthodontic component, comprising a rigid backbone polymer, the rigid backbone polymer at least partially comprising a first arylene or heteroarylene moiety joined to a second arylene or heteroarylene moiety by a covalent bond between adjoining ring carbon atoms of the arylene or heteroarylene moieties.

2. The orthodontic component of claim 1, wherein the polymer is used in a neat form and the component has isotropic properties.

3. The orthodontic component of claim 1, further comprising reinforcing fibers.

4. The orthodontic component of claim 1, further comprising filler.

5. The orthodontic component of claim 1, further comprising a non-rigid backbone polymer.

6. The orthodontic component of claim 1, in the form of a wire having a shape capable of providing a good fit in an orthodontic bracket.

7. The orthodontic component of claim 1 comprising a 1,4 covalent bond.

8. The orthodontic component of claim 1 wherein the rigid backbone polymer comprises a plurality of covalent bonds and wherein at least about 95% of the covalent bonds are substantially parallel to each other.

9. The orthodontic component of claim 1 wherein the rigid backbone polymer comprises the following structure:

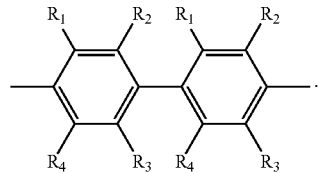

10. The orthodontic component of claim 1 wherein the rigid backbone polymer comprises the following structure:

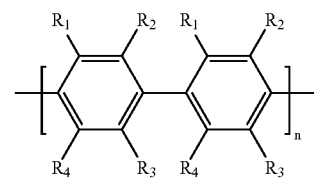

and n is an integer from 2 to about 8.

11. The orthodontic component of claim 1 wherein the rigid backbone polymer comprises at least one of a compatibilizing side group or a solubilizing side group.

12. The orthodontic component of claim 11, wherein the side group reacts with a non-rigid backbone polymer and thereby reduces phase separation.

13. An orthodontic component, comprising a thermoplastic polymer and without a reinforcing agent, wherein the thermoplastic polymer has a tensile strength of at least about 150 MPa and a tensile modulus of at least about 4 GPa.

14. The orthodontic component of claim 13, wherein the polymer in the neat resin form has an elastic deformation of at least about 30.

15. The orthodontic component of claim 13, wherein the polymer has a tensile strength of at least about 200 MPa and a tensile modulus of at least about 8 GPa.

16. The orthodontic component of claim 13, having a refractive index of about 1.66 to about 1.70.

17. The orthodontic component of claim 13, further comprising a reinforcing agent.

18. The orthodontic component of claim 13, consisting essentially of the thermoplastic polymer and no more than 5 percent by component weight of a reinforcing agent.

19. The orthodontic component of claim 13, selected from a force delivery component, a wire, an attachment and an auxiliary.

20. The orthodontic component of claim 13, comprising a wire wherein the wire has a cross section that is not circular and not quadrilateral.

21. The orthodontic component of claim 13, comprising a wire wherein the wire has a cross sectional shape selected from a circle, a portion of a circle delineated by two radii of the circle, a polygon, an "I" shape, a "C" shape, an "L" shape, a "T" shape or a combination thereof.

22. The orthodontic component of claim 13, comprising a bracket having a slot, wherein the slot is configured to interengage with wires of different cross-sectional shapes to provide a good fit.

23. The orthodontic component of claim 13, comprising a wire, wherein the wire has a different cross section at different points along its length.

24. The orthodontic component of claim 13, having a Rockwell B hardness of at least about 75.

25. The orthodontic component of claim 13, having a pencil hardness of at least about 7H.

26. The orthodontic component of claim 13, comprising at least a second polymer material.

27. The orthodontic component of claim 13, consisting essentially of the thermoplastic polymer.

28. The orthodontic component of claim 13, wherein the thermoplastic polymer is in the form of a coating over at least part of a core.

29. The orthodontic component of claim 13 wherein the thermoplastic polymer is used in a neat form.

30. The orthodontic component of claim 13, further comprising a reinforcing agent.

31. An orthodontic component, comprising a thermoplastic polymer, wherein the thermoplastic polymer has an unreinforced tensile strength of at least about 150 MPa and an unreinforced tensile modulus of at least about 4 GPa.

32. The orthodontic component of claim 31, wherein the thermoplastic polymer comprises a first arylene or heteroarylene moiety joined to a second arylene or heteroarylene moiety by a covalent bond between adjoining ring carbon atoms of the arylene or heteroarylene moieties.

* * * * *